United States Patent [19]

Theeuwes et al.

[11] 4,058,122
[45] * Nov. 15, 1977

[54] OSMOTIC SYSTEM WITH LAMINATED WALL FORMED OF DIFFERENT MATERIALS

[75] Inventors: Felix Theeuwes, Los Altos; Atul D. Ayer, Belmont, both of Calif.

[73] Assignee: Alza Corporation, Palo Alto, Calif.

[*] Notice: The portion of the term of this patent subsequent to Feb. 22, 1994, has been disclaimed.

[21] Appl. No.: 750,698

[22] Filed: Dec. 15, 1976

Related U.S. Application Data

[63] Continuation of Ser. No. 654,195, Feb. 2, 1976, Pat. No. 4,008,719.

[51] Int. Cl.² ............................................. A61M 31/00
[52] U.S. Cl. ..................................... 128/260; 424/22
[58] Field of Search ............... 128/260, 261, 268, 271, 128/272; 424/19, 22

[56] References Cited

U.S. PATENT DOCUMENTS

| | | | |
|---|---|---|---|
| 3,737,521 | 6/1973 | Born | 424/22 |
| 3,811,444 | 5/1974 | Heller | 128/260 |
| 3,832,458 | 8/1974 | Merrill | 424/19 |
| 3,845,770 | 11/1974 | Theeuwes et al. | 128/260 |
| 3,916,899 | 11/1975 | Theeuwes et al. | 128/260 |
| 3,948,254 | 4/1976 | Zaffaroni | 128/260 |
| 3,961,628 | 6/1976 | Arnold | 128/260 |
| 3,987,790 | 10/1976 | Eckenhoff et al. | 128/260 |
| 4,008,719 | 2/1977 | Theeuwes et al. | 128/260 |

*Primary Examiner*—Aldrich F. Medbery
*Attorney, Agent, or Firm*—Paul L. Sabatine; Edward L. Mandell; Thomas E. Ciotti

[57] ABSTRACT

An osmotic system for delivering an agent is disclosed. The system comprises a wall surrounding a compartment and has a passageway for delivering agent from the compartment. The wall is formed of a laminae comprising a lamina consisting of a multiplicity of materials in laminar arrangement with a lamina consisting of a material or of a multiplicity of materials to provide a laminated wall that is permeable to agents and maintains its integrity during the delivery of agent. The compartment contains an agent that is soluble in an external fluid and exhibits an osmotic pressure gradient across the wall against the fluid, or the agent has limited solubility in the fluid and is mixed with an osmotically effective compound soluble in the fluid and exhibits an osmotic pressure gradient across the wall against the fluid. In operation, agent is released from the system by fluid being imbibed through the wall into the compartment at a rate controlled by the permeability of the wall and the osmotic pressure gradient across the wall producing a solution containing agent, or a solution of compound containing agent which solution in either operation is released through the passageway at a controlled and continuous rate over a prolonged period of time.

15 Claims, 11 Drawing Figures

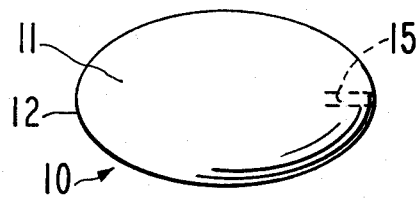
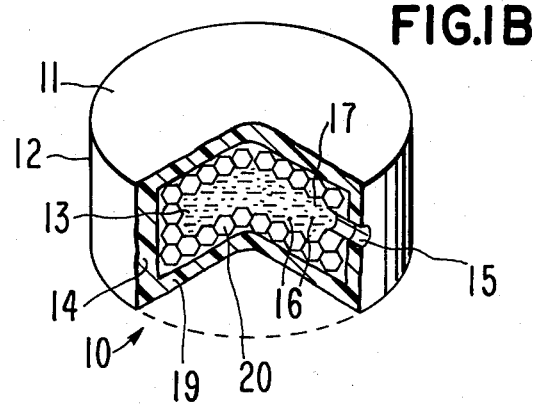
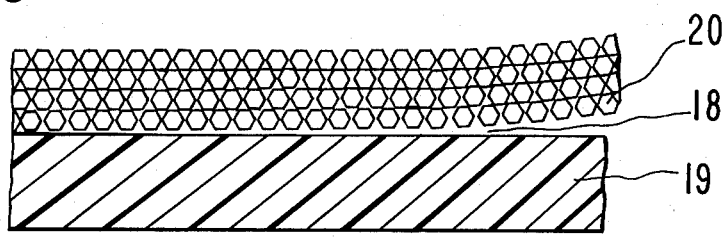
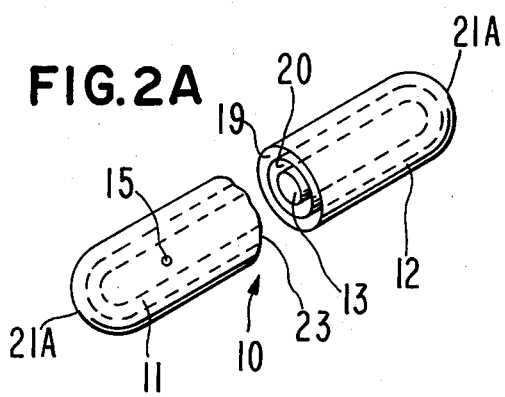
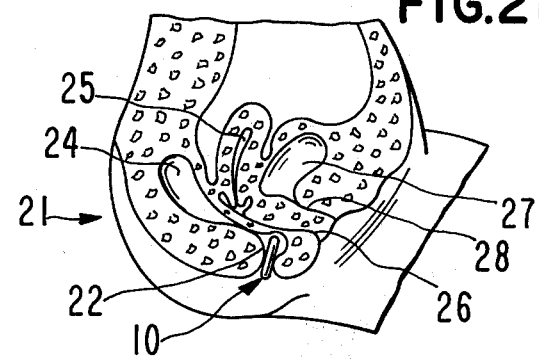
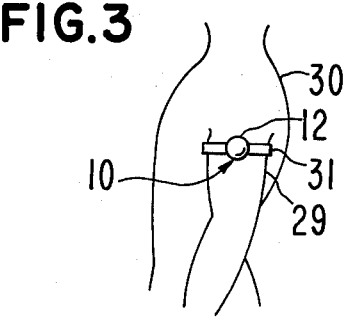
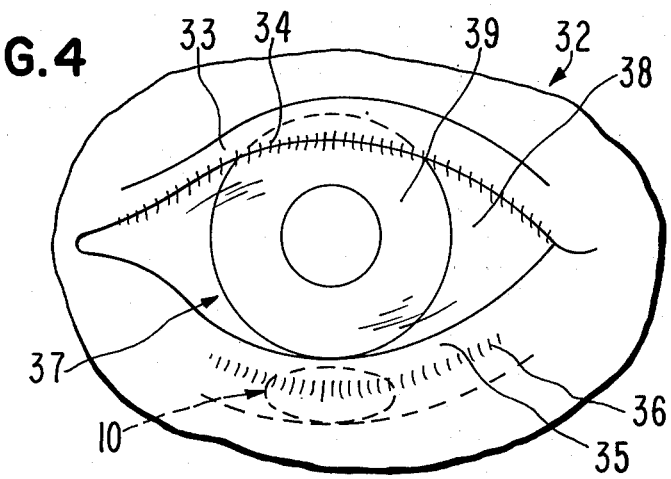

OSMOTIC SYSTEM WITH LAMINATED WALL FORMED OF DIFFERENT MATERIALS

CROSS-REFERENCE TO RELATED APPLICATION

This application is a continuation of U.S. Patent application Ser. No. 654,195 filed on Feb. 2, 1976 now U.S. Pat. No. 4,008,719 issued on Feb. 22, 1977, which applications are assigned to the ALZA Corporation of Palo Alto, Ca.

FIELD OF THE INVENTION

This invention pertains to an osmotic system in the form of an osmotic device. More particularly, the invention relates to an osmotic system comprising a laminated wall formed of at least one semipermeable lamina consisting of a multiplicity of materials laminated to a semipermeable lamina consisting of a material or of a multiplicity of materials for delivering an active agent at a controlled and continuous rate over a prolonged period of time.

BACKGROUND OF THE INVENTION

Osmotic systems in the form of osmotic devices for delivering a beneficial agent to an environment of use are known to the art in U.S. Pat. Nos. 3,845,770 and 3,916,899. The systems disclosed in these patents are made with a wall that surrounds a compartment containing an agent. The wall is permeable to an external fluid, substantially impermeable to agent, and has a passageway for delivering agent. These systems are extraordinarily effective for delivering an agent that is soluble in the fluid and exhibits an osmotic pressure gradient across the wall against the fluid, and also for delivering an agent that has limited solubility in the fluid and is mixed with an osmotically effective compound that is soluble in the fluid and exhibits an osmotic pressure gradient across the wall against the fluid. The systems release agent by fluid being continuously imbibed through the wall into the compartment at a rate determined by the permeability of the wall and the osmotic pressure gradient across the wall to produce a solution of soluble agent, or a solution of soluble compound containing agent which solution in either operation is dispensed at a controlled and continuous rate over a prolonged period of time. While the above systems represent an outstanding and pioneer advancement in the delivery art, and while they are useful for dispensing innumerable agents to an environment of use, it has now been found the systems can have a laminated wall that unexpectedly improves the usefulness and integrity of the systems.

That is, the systems can have a laminated wall that permits properties such as permeability to fluids, impermeability to agents and compounds, and physical and chemical integrity be selected independently, and also have the mode of agent release made programmable based on the laminae comprising the wall. For example, the wall can comprise a laminae consisting of a lamina facing a compartment and a lamina facing an environment with each possessing different properties. The lamina facing the compartment housing ingredients such as agents, osmotic compounds and solutions thereof, that can slowly attack and cause the lamina to loose its integrity can be made inert by formulating it with materials resistant to attack therefrom, while the lamina facing the environment can be formed of different materials inert to the environment, and which lamina optionally is not contacted by the ingredients, and if it is exposed thereto, it does not interact therewith.

OBJECTS OF THE INVENTION

Accordingly, it is an immediate object of this invention to provide an osmotic system for the controlled and continuous delivery of an active agent over a prolonged period of time which system is an improvement over the systems known to the prior art.

Another object of the invention is to provide an osmotic system comprising a laminated wall formed of at least two laminae made of a multiplicity of materials which laminae maintain their physical and chemical integrity during the controlled and continuous dispensing of an agent over a prolonged period of time.

Yet another object of the invention is to provide an osmotic system comprising a laminated wall comprising a semipermeable lamina formed of a multiplicity of materials and a semipermeable lamina formed of a material which laminae are non-erodible and inert during the dispensing of an agent.

Still a further object of the invention is to provide an osmotic system having a wide spectrum of laminated walls in which properties such as fluid transmission rate and resistance to attack may be independently controlled and regulated to a particular application.

Still another object of the invention is to provide an osmotic system having a laminated wall that has a programmable flux rate to fluids, a high degree of exclusion towards agents and compounds, and resistance to hydrolysis over a wide pH range.

Still another object of the invention is to provide an osmotic system for administering drug where the dose administered contains the intended quantity and is administered at the correct rate to ensure the required onset, intensity and duration of biological response.

Yet still another object of the invention is to provide an osmotic system for administering a drug wherein the drug is administered as a solution eliminating in vivo dissolution as a controlling mechanism, and providing the drug in the most readily available form for absorption.

Still another object of the invention is to provide an osmotic therapeutic system having a laminated wall that makes the system programmable and versatile, and allows a wider control over the rate drug is released to a drug receptor site.

Other objects, features and advantages of the invention will be more apparent to those skilled in the art from the following detailed specification, taken in conjunction with the drawings and the accompanying claims.

STATEMENT OF THE INVENTION

This invention concerns an osmotic system for dispensing an agent. The system comprises a laminated wall surrounding a compartment and has a passageway for dispensing agent. The compartment contains an agent that is soluble in an external fluid and exhibits an osmotic pressure gradient across the wall against the fluid, or it contains a mixture of agents having limited solubility in the fluid and an osmotically effective compound soluble in fluid that exhibits an osmotic pressure gradient across the wall against the fluid. The wall is permeable to fluid, impermeable to agent and compound, and inert towards agent, compound and the environment of use. The wall comprises at least two lamina, one formed of a semipermeable lamina material blended with other lamina forming materials, and one formed of a semipermeable lamina material, or of a semipermeable lamina material blended with other lamina forming materials. Agent is released from the system by fluid being imbibed through the laminated wall into the compartment at a rate controlled by the permeability of the wall and the pressure gradient across the wall producing a solution containing agent that is released through the passageway at a controlled and continuous rate over a prolonged period of time.

BRIEF DESCRIPTION OF THE DRAWINGS

In the drawings, which are not drawn to scale, but are set forth to illustrate various embodiments of the invention, the figures are as follows:

FIG. 1A is a view of an osmotic therapeutic system designed for orally delivering a beneficial agent;

FIG. 1B is a view of the osmotic therapeutic system of FIG. 1A in opened section illustrating a laminated wall and a compartment of the system;

FIG. 1C is a perspective view of a portion of the laminated wall of FIG. 1B with one end peeled open showing the semipermeable laminae that form the wall;

FIG. 2A is a view of an osmotic therapeutic system manufactured for administering drug in the anus with the system illustrated in halved section for elucidating structural details thereof;

FIG. 2B is a view of the osmotic therapeutic system of FIG. 2A osmotically administering drug in the environment of use;

FIG. 3 is a view of an osmotic therapeutic system manufactured for topically administering a drug;

FIG. 4 is a front view of the human eye illustrating an osmotic ocular system in operative position in the eye;

In the drawings and specification, like parts in related figures are identified by like numbers. The terms appearing earlier in the specification and in the description of the drawings, as well as embodiments thereof, are further detailed elsewhere in the disclosure.

DETAILED DESCRIPTION OF THE DRAWINGS

Figure 5:
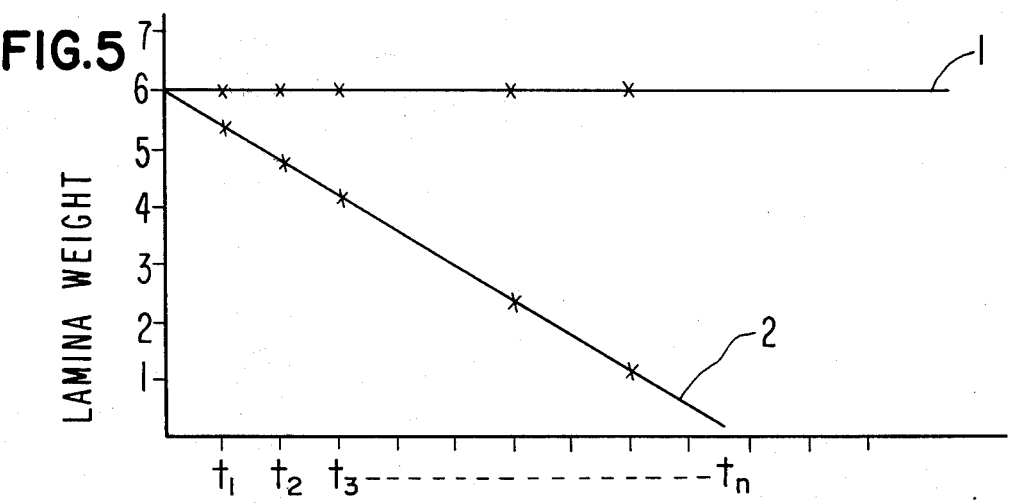
FIG. 5 is a graph comparing a lamina that is inert with a lamina that slowly loses its integrity in the presence of agent.

Turning now to the drawings in detail, which are examples of various osmotic systems of the invention, and which examples are not to be construed as limiting, one embodiment of an osmotic system is indicated in FIGS. 1A, 1B and 1C considered together by the numeral 10. In FIGS. 1A and 1B an osmotic system 10 in the form of an oral, osmotic therapeutic system is comprised of a body 11 having a semipermeable laminated wall 12 that surrounds a compartment 13, seen in FIG. 1B in opened section with a portion of wall 12 removed at 14. System 10 has a passageway 15 in wall 12 that extends through 12 and communicates with compartment 13 and the exterior of system 10. Compartment 13, as seen in FIG. 1B, is a means for containing a beneficial agent 16 that is soluble in an external fluid and exhibits an osmotic pressure gradient across wall 12 against an external fluid or, compartment t3 optionally contains a mixture of agents 16 with at least one agent exhibiting an osmotic pressure gradient. In another embodiment, compartment 13 contains an agent that has limited solubility or is substantially insoluble in the external fluid and is mixed with an osmotically effective compound 17 that is soluble in the external fluid and exhibits an osmotic pressure gradient across wall 12. Compartment 13 optionally contains other compounds such as a surfactant for wetting the agent, a gelling or suspending agent to displace the active agent from the compartment, or a non-toxic dye for identifying agent 16 and for making release of agent 16 visible to the unaided eye.

Wall 12, as seen in FIG. 1C, represents a section removed from system 10 of FIG. 1B, and it is separated at 18 for illustrating the laminated structure of wall 12. Wall 12 comprises a lamina consisting of an exterior, semipermeable lamina 19 and an interior semipermeable lamina 20. Lamina 19, in one embodiment, is a composite comprising at least two materials blended to form a lamina that is, (a) permeable to the passage of an external fluid, (b) maintains its physical and chemical integrity in the environment of use, and is more particularly substantially non-erodible and inert in the environment, (c) provides mechanical support for other laminae comprising wall 12, and (d) optionally is substantially impermeable to compounds present in the environment of use. Lamina 19, in another embodiment is formed of a semipermeable material and has the properties described in (a) through (d).

Lamina 20, in one embodiment, is a composite comprising at least two materials blended to form a semipermeable lamina that is, (e) permeable to the passage of an external fluid, (f) substantially impermeable to the passage of agent and compound present in the compartment, (g) maintains its physical and chemical integrity in the presence of agent and more particularly is substantially non-erodible and inert in the presence of agent, (h) provides mechanical support for other laminae forming wall 12, and (i) it is substantially impermeable to compounds present in the environment of use. Lamina 20, in another embodiment, is formed of a single semipermeable material having the properties of (e) through (i). Also, according to the instant invention, at least one of laminae 19 or 20 is a composite endowed with the above described properties, with the lamina positioned facing the compartment in a presently preferred embodiment more hydrophobic, more inert, having a higher degree of agent and compound rejection, and having a decreased permeability to the passage of an external fluid. While laminae 19 and 20 in a presently preferred lamination were described with lamina 20 positioned facing compartment 13 and lamina 19 positioned distant from compartment 13, it is understood for other embodiments and applications, lamina 20 can be the exterior surface of system 10 distant from compartment 13, and lamina 19 can be the interior surface of laminated wall 12. A detailed description of laminae forming materials, agents and compounds is presented later in the specification.

In operation, system 10 in one embodiment releases agent 16 contained in compartment 13 and soluble in the external fluid by fluid being inbibed into compartment 13 in a tendency towards osmotic equilibrium at a rate controlled by the permeability of laminated wall 12 and the osmotic pressure gradient across wall 12 to continuously dissolve agent 16 which is osmotically pumped from system 10 through passageway 15 at a controlled and continuous rate over a prolonged period of time. System 10, in another emboidment, releases agent 16 that has limited solubility in the fluid and is mixed with an osmotically effective compound by fluid being imbibed through wall 12 into compartment 13 in a tendency towards osmotic equilibrium at a rate controlled by the permeability of wall 12 and the osmotic pressure gradient across wall 12 to continuously dissolve the osmotically effective compound to form a solution containing agent that is released from system 10 through passageway 15 at a controlled and continuous rate over a prolonged period of time.

Osmotic system 10 of FIGS. 1A through 1C can be made into many useful embodiments including the presently preferred embodiment for oral use. The oral system is useful for releasing in the gastrointestinal tract either a locally or systemically acting agent over a prolonged period of time. Osmotic, oral therapeutic system 10 can have various conventional shapes and sizes such as round with a diameter of 3/16 inches to ½ inches, or it can be shaped like a capsule having a range of sizes from triple zero to zero, and from 1 to 8.

FIGS. 2A and 2B represent another osmotic system 10 manufactured according to the invention for administering a drug to a drug receptor. In the illustrated embodiment, system 10 is designed for placement and drug release in an anus 22 of a patient 21. System 10 consists of a relatively long and relatively small diameter tubular body 11 made with rounded ends 21a for easily placing system 10 in anus 22, as seen in FIG. 2B. System 10, seen in halved-section at 23, is structurally identical to system 10 described above and it operates in a like manner. System 10 is comprised of a laminated wall 12 formed of a pair of laminae 19 and 20 surrounding and forming compartment 13 for containing a drug, not shown. A passageway 15 connects compartment 13 with the exterior of system 10 for releasing a locally or systemically acting drug to anus 22. System 10 in another embodiment can be sized, shaped and adapted for placement in vagina 26 of patent 21 for releasing a drug or fragrence in vagina 26. Other anatomical features of patient 21 illustrated in FIG. 2B are rectum 24, bladder 27 and urethra 28.

FIG. 3 represents another system 10 designed for administering a drug. In FIG. 3, system 10 is mounted on a drug receptor site 29, an arm of human 30, for administering drug locally or systemically by absorption or drug penetration. System 10 is comprised of non-toxic laminated wall 12 formed of a pair of semipermeable laminae 19 and 20 that surrounds and forms a circle shaped compartment. The compartment contains an agent, or optionally a mixture of agent and an osmotically effective compound. Wall 12 has a curvature that corresponds to the curvature of site 29 for proper placement on site 29. System 10 has a passageway positioned on its under surface for releasing drug to site 29. System 10 is equipped with a band and buckle 31 that circles the arm for holding system 10 thereon. System 10 is structured and operates as previously described, and it administers drug at a controlled and continuous rate to site 29 for a prolonged period of time.

Referring to FIG. 4, an ocular therapeutic system 10 is seen in eye 32 for administering drug at an osmotically metered dosage rate thereto. In FIG. 4, eye 32 is comprised of an upper eyelid 33 with eyelashes 34, a lower eyelid 35 with eyelashes 36, and an eyeball 37 covered for the greater part by sclera 38 and at its center area by cornea 39. Eyelids 33 and 35 are lined with an epithelial membrane or palpebral conjunctiva, sclera 38 is lined with a bulbar conjunctiva that covers the exposed surface of eyeball 37, and cornea 39 is covered with a transparent epithelial membrane. The portion of the conjunctiva which lines upper eyelid 33 and the underlying portion of the bulbar conjunctiva defines an upper cul-de-sac, while that portion of the palpebral conjunctive which lines the lower eyelid 35 and the underlying portion of the bulbar conjunctiva defines a lower cul-de-sac. Ocular osmotic system 10, seen in broken lines, is shaped, sized and adapted for placement in the upper or lower cul-de-sac. System 10 is seen in the lower cul-de-sac and it is held in place by the natural pressure of lower eyelid 35. System 10 contains an ophthalmic drug for release to eye 32 at a controlled and continuous rate over a prolonged period of time.

Ocular system 10 can have any geometric shape that fits comfortably in the cul-de-sac. Typical shapes include ellipsoid, bean, banana, circular, rectangular, doughnut, crescent and half-ring shaped systems. In cross-section, the system can be doubly convex, concavo-convex, rectangular and the like, as the device in use will tend to conform to the shape of the eye. The dimensions of an ocular system can vary widely with the lower limit governed by the amount of drug to be supplied to the eye as well as by the smallest sized system that can be placed into the eye. The upper limit on the size of the system is governed by the space limitation in the eye consistent with comfortable retention in the eye. Satisfactory systems generally have a length of 4 to 20 millimeters, a width of 1 to 15 millimeters. The ocular system can contain from 0.15 micrograms to 100 milligrams of drug, or more, and it is made from non-erodible and inert materials that are compatible with the eye and its environment.

While FIGS. 1 through 4 are illustrative of various systems that can be made according to the invention, it is to be understood these systems are not to be construed as limiting, as the systems can take a wide variety of shapes, sizes and forms for delivering agent to different environments of use. For example, the systems include buccal, intramuscular implant, nose, artificial gland, anus, rectum, cervical, intrauterine, arterial, venous, vaginal, and ear systems. The systems also can be adapted for delivering an active agent in streams, aquariums, fields, factories, reservoirs, laboratory facilities, hot houses, transportation means, navel means, air and military means, hospitals, veterinary clinics, nursing homes, chemical reactions, and other environments of use.

DETAILED DESCRIPTION OF THE INVENTION

In accordance with the practice of the invention, the terms used herein denote the following: the terms "osmotic delivery system" and "osmotic delivery system in the form of an osmotic device" are deemed as functional equivalents and generically they are osmotic devices. These terms also include "osmotic therapeutic systems" and "systems". The phrase "maintains its physical and chemical integrity" means the laminated wall and the laminae keep their constitution and general preselected design and shape in the environment of use and in the presence of agent during the period of agent release even though the system may be flexible and resilient. The terms "non-erodible", "resist erosion", "resist bioerosion", and "inert" mean the laminated wall and the laminae are substantially resistant and free from chemical, enzymatic and biological attack and reaction in the environment of use and in the presence of agent. The expression "laminated wall" means the wall of the system is comprised of at least two laminae in laminar arrangement acting in concert to form an integral, unit wall that does not separate into laminae during the operative history of the system. The term "composite" means a lamina formed of a blend of materials that produce an operative, semipermeable lamina useful for manufacturing a laminated wall. The expression "formed of a multiplicity of materials" means a semipermeable lamina formed of at least two materials that produce a composite lamina. The phrases "a semipermeable lamina forming material", or "a single semipermeable polymeric lamina forming material" means this lamina is formed of a semipermeable homopolymer or of a semipermeable copolymer. The term "hydrophobic" means a semipermeable polymer when placed in water for 24 hours does not absorb it in an amount exceeding 10 percent of its dry weight.

Further, in accordance with the practice of the invention, it has now been discovered that osmotic delivery systems can be manufactured with a laminated wall comprised of at least two different laminae selected from the group consisting of laminae formed of a material and laminae formed of a blend of materials. Materials suitable for forming laminae consisting of a single material are generically polymeric materials. The polymeric materials are homopolymers and copolymers and they include materials known as semipermeable, osmosis and reverse osmosis materials. Laminae 19 and 20 when formed of a material are independently selected from semipermeable homopolymers and semipermeable copolymers which generically include polysaccharides comprised of anhydroglucose units. In one embodiment, the polysaccharides are cellulose esters having a degree of substitution, D.S., on the anhydroglucose unit from greater than 0 up to 3 inclusive. By "degree of substitution" as used herein is meant the average number of hydroxyl groups on the anhydroglucose unit of the polymer replaced by a substituting group. Exemplary materials are represented by Formula 1:

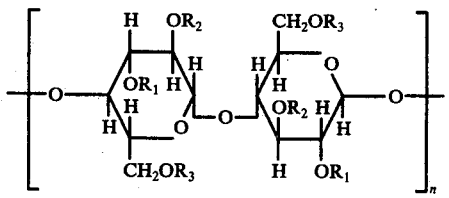 (1)

wherein $R_1$, $R_2$ and $R_3$ are the same or different and they are selected from the group consisting of hydrogen and acyl,

with at least one or all of $R_1$, $R_2$ and $R_3$ in the anhydroglucose unit either partially or completely substituted with the acyl moiety. The acyl moiety at $R_1$, $R_2$ and $R_3$ can be the same or different; and, $R_4$ is a member selected from the group consisting of hydrogen, alkyl groups of the straight or branched chain type having from 1 to 20 carbons and alkenyl groups that are straight or branched and have from 2 to 20 carbon atoms. Typical acyl moieties include alkanoyl and alkenoyl such as formyl, acetyl, propionyl, butyryl, hexanoyl, heptanoyl, octanoyl, undecanoyl, lauroyl, palmitoyl, stearoyl, oleoyl, and isomeric forms thereof; and n in a presently preferred embodiment is a positive number greater than 5.

Representative materials embraced by Formula 1 include polymeric cellulose esters and copolymeric cellulose esters such as mono, di, and tricellulose acylates. Exemplary polymers include cellulose acetate having a D.S. up to 1 and an acetyl content of up to 21%; cellulose diacetate having a D.S. of 1 to 2 and an acetyl content of 21 to 35%; cellulose triacetate having a D.S. of 2 to 3 and an acetyl content of 35 to 44.8%; cellulose proprionate having a D.S. of 1.8 and a propionyl content of 38.5%; cellulose acetate propionate having an acetyl content of 1.5 to 7% and a propionyl content of 39 to 42%; cellulose acetate propionate having an acetyl content of 2.5 to 3%, an average combined propionyl content of 39.2 to 45% and a hydroxyl content of 2.8 to 5.4%; cellulose acetate butyrate having a D.S. of 1.8, an acetyl content of 13 to 15%, and a butyryl content of 34 to 39%; cellulose acetate butyrate having an acetyl content of 2 to 29.5%, a butyryl content of 17 to 53%, and a hydroxyl content of 0.5 to 4.7%; cellulose triacylates having a D.S. of 2.9 to 3 such as cellulose trivalerate, cellulose trilaurate, cellulose tripalmate, cellulose trisuccinate, cellulose triheptylate, cellulose tricaprylate, cellulose trioctanoate, and cellulose tripropionate; cellulose diesters having a lower degree of substitution and prepared by the hydrolysis of the corresponding triester to yield cellulose diacylates having a D.S. of 2.2 to 2.6 such as cellulose disuccinate, cellulose dipalmitate, cellulose dioctanoate, cellulose dicaprylate, and cellulose dipentanate; and esters prepared from acyl anhydrides or acyl acids in an esterification reaction to yield esters containing different acyl groups attached to the same cellulose polymer such as cellulose acetate valerate, cellulose acetate succinate, cellulose propionate succinate, cellulose acetate octanoate, cellulose valerate palmitate, cellulose acetate palmitate, and cellulose acetate heptanoate. Generally, materials useful for forming the laminated wall and the laminae will have a fluid permeability of $10^{-5}$ to $10^{-1}$ (cc mil/cm$^2$ hr atm), expressed per atmosphere (atm) of hydrostatic or osmotic pressure difference across the wall or lamina at the temperature of use while possessing a high degree of impermeability to solute are useful for the purpose of the invention. The polymers described above are known to the art or they can be prepared according to the procedures in *Encyclopedia of Polymer Science and Technology*, Vol. 3, pages 325 to 354, 1964, published by Interscience Publishers Inc., New York.

Laminae 19 and 20 also can be independently selected from semipermeable homopolymers and semipermeable copolymers embraced by Formula 2 as follows:

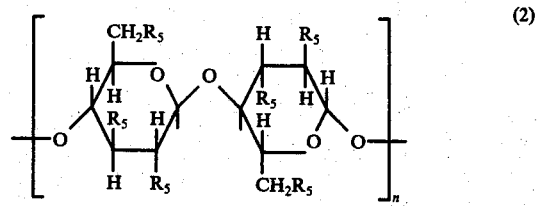 (2)

wherein $R_5$ is a member selected from the group consisting of hydroxyl; alkoxy; alkoxy substituted with a member selected from the group consisting of alkyl, alkoxy, halogen and cyano; alkylcarbonate; alkylcarbamate; alkylsulfonate; alkylsulfamate; oxalkyleneoxycarboalkyl; acyloxy including alkanoyloxy, alkenoyloxy and aroyloxy; alkanoyloxy substituted with an alkoxy, halogen, carboalkyl, carboalkoxy and cyanoalkoxy; aroyloxy substituted with a halo, carboxy, carboalkyl and cyano; furoyloxy, and $n$ is a positive integer greater than 5, usually 10 to $3 \times 10^6$.

Exemplary groups representative of $R_5$ of Formula 2 are as follows: by "alkyl" is meant straight or branched chain alkyl radicals of 1 to 20 carbon atoms inclusive, such as methyl, ethyl, n-propyl, iso-propyl, n-butyl, sec-butyl, pentyl, neo-pentyl, n-hexyl, iso-hexyl, heptyl, 4,4-dimethyl pentyl, 2,2,4-trimethylpentyl, and nonyl. By "alkenyl" is meant straight or branched chain alkenyl groups of 2 to 20 carbons such as 1-propenyl, 2-propenyl or allyl, 1-butenyl, 2-butenyl, 1-pentenyl, and the corresponding positional isomers such as 1-isobutenyl, 2-isobutenyl, 2-sec-butenyl, 2-methyl-1-butenyl, 2-methyl-2-pentyenyl and 2,3-dimethyl-3-hexenyl. The term "alkoxy" as used for $R_5$ included the straight and branched chain alkoxy groups having 1 to 20 carbons inclusive, for example, methoxy, ethoxy, propoxy, butoxy, n-pentoxy, n-hexoxy, isopropoxy, 2-butoxy, isobutoxy, 3-pentoxy, and n-octoxy. Exemplary halogen include fluorine, chlorine and bromine. Exemplary aryl include phenyl and naphthyl. Exemplary alkylene as a linking moiety within a substituent are alkylenes of 2 to 10 carbons such as 1,2-ethylene, 1,3-propylene, 1,2-propylene, 1,4-butylene, 1,5-pentylene, 1,6-hexylene, 1,7-heptylene and 1,10-decylene. Exemplary alkanoyloxy, alkenoyloxy and aroyloxy include formyloxy, acetyloxy, propionyloxy, valeryloxy, heptanoyloxy, octanoyloxy, undecanoyloxy, lauroyloxy, palmitoyloxy, stearoyloxy, oleoyloxy, acryloyloxy, methacryloyloxy, crotomyloxy, 3-butenoyloxy, benzoyloxy, phenylacetyloxy, cinnamoyloxy, napththoyloxy, p-ethoxybenzyloxy, alloxyphenylacetyloxy, furoyloxy, p-nitrobenzoyloxy and chlorophenoxyacetyloxy.

The laminae forming materials embraced by Formula 2 include polysaccharide materials having a degree of substitution on the anhydroglucose unit greater than from 0 up to 3 inclusive with the substituents $R_5$ the same or different and bonded to a common mer. The materials can be polymeric cellulose esters or polymeric cellulose ethers. The monomeric unit can be substituted with like ester groups, with different ester groups, with like ether groups, with different ether groups and with different ester and ether groups bonded to the same mer to give a homopolymer or copolymer. Typical materials represented by Formula 2 include cellulose acetate acetoacetate, cellulose acetate chloroacetate, cellulose acetate furoate, dimethoxyethylcellulose acetate, cellulose acetate carboxymethoxypropionate, cellulose acetate phthalate, cellulose butyrate naphthylate, cellulose acetate benzoate, methylcellulose acetate, methylcyanoethyl cellulose, cellulose acetate methoxyacetate, cellulose acetate, cellulose acetate ethoxyacetate, cellulose acetate dimethylsulfamate, ethylcellulose dimethylsulfamate, cellulose acetate p-toluene sulfonate, cellulose acetate methylsulfonate, cellulose acetate dipropylsulfamate, cellulose acetate butylsulfonate, cellulose acetate dimethylaminoacetate, cellulose acetate ethyloxalate, cellulose acetate laurate, cellulose butyrate furoate, cellulose stearate, cellulose resinate, cellulose acetate methylcarbonate, cellulose acetate ethylcarbonate, cellulose acetate methylcarbamate, and cellulose acetate ethylcarbamate.

The semipermeable laminae forming materials also include cellulose ethers such as alkylcellulose, methylcellulose, ethylcellulose, ethylmethylcellulose, hydroxyethylcellulose, hydroxypropylcellulose, hydroxyethyl methylcellulose, hhdroxypropyl methylcellulose, ethylhydroxy ethylcellulose, hydroxybutyl methylcellulose, cyanoethylcellulose, benzylcellulose, sodium carboxymethylcellulose, sodium carboxymethylhydroxy ethylcellulose, carbamoylethylcellulose, carboxyethylcellulose, phenylcellulose, benzylhydrylcellulose, tritylcellulose, hexylpropylcellulose, carboxylbenzyl cellulose and 2-carboxylbenzoyloxy propylcellulose. Methods for preparing the cellulose ethers are disclosed in *Encyclopedia of Polymer Science and Technology*, Vol. 3, pages 459 to 549, 1964, published by Interscience Publishers, Inc., New York.

Other semipermeable materials useful for forming laminae include acylated polysaccharides and acylated starches such as agar-agar acetate, acylated alginates, amylose triacetate, beta glucan acetate, beta glucan triacetate, acetyl alginate, triacetate of locust bean gum, alkanoyl carrageenin, acylated tragacanth, esterified gum karaya, cellulose derivatives substituted with an inorganic moiety such as a nitro group, hydroxylated ethylene vinylacetate, aromatic nitrogen containing polymeric materials that exhibit permeability to aqueous fluids and substantially no passage to solute, semipermeable membranes made from polymeric epoxides, copolymers of alkylene oxides and alkyl glycidyl ethers, polyvinyl acetate, cross-linked polyvinyl acetate, polyurethanes, film forming materials as disclosed by Loeb and Sourirajan in U.S. Pat. No. 3,133,132, cross-linked derivatives of polyvinyl alcohol, polyvinyl butyrate, ionically associated polyelectrolytes formed by the coprecipitation of a polycation and a polyanion as described in U.S. Pat. Nos. 3,276,586; 3,541,005; 3,541,006; 3,546,142; and 3,173,876; polystyrene derivatives such as poly(sodium styrene sulfonate) and poly(vinylbenzyltrimethyl ammonium chloride), polyesters, polyamides and polyacrylates. These semipermeable materials and other semipermeable materials are known to the art and disclosed in *Handbook of Common Polymers* by Scott, J. R. and Roff, W. J., 1971, published by CRC Press, Cleveland, Ohio.

Further, in accordance with the invention, laminae 19 and 20 when formed of a blend of materials, consists independently selected from composite lamina forming materials with each lamina comprised of, (1) at least one semipermeable lamina forming material permeable to the passage of fluid and substantially impermeable to agent and other compounds blended with at least one or more of the following lamina forming materials, (2) a stabilizing material that imparts physical and chemical integrity to the lamina, and more particularly gives the lamina inertness towards agents, compounds and solutions thereof, and to compounds present in the environment of use, (3) a flux regulator that governs the permeability of fluid through the lamina, (4) a plasticizer that gives flexibility to the lamina, and (5) a dispersant useful for blending the materials into an operative integral composite lamina. The laminated wall's integrity or inertness to agents in the compartment, and to fluids and other compounds in the environment of use can be precisely regulated by selecting the ingredients blended into composite laminae forming the laminated wall of the system. The fluid permeability of the laminated wall can be regulated in a like manner.

The composite laminae will in a presently preferred embodiment, include at least one of the semipermeable materials embraced by Formula 1. Laminae 19 and 20 also can include a stabilizing material identified above as 2. This latter material is a different material than the laminae forming material and it is selected from the materials embraced by Formula 1 and included therewith, or the materials embraced by Formula 2 and included therewith. Also, the semipermeable materials of Formula 2 and included therewith can be used to form composite laminae when blended with stabilizing materials. Criterion that can be used for selecting laminae forming materials, stabilizing materials, and other materials used to form blends are presented later in the specification.

Suitable laminae for manufacturing laminated osmotic systems can be selected according to the criterion disclosed in U.S. Pat. No. 3,845,770 and 3,916,899. This criterion consists in first calculating for a laminate that is to be selected, the permeability to fluid necessary to deliver an amount of agent $Q_p$, in mg, in time $t$, in hours, from a system having a total laminated area A, in cm$^2$, a laminated thickness $h$, in mils, with the agent having a solubility in the fluid S, in mg/ml (solution), and the agent having an osmotic pressure in the device of $\pi$, in atm. The value $k$ is expressed in units (cm$^3$/cm$^2$).(mil/hr.atm) and it is calculated from Equation 1.

$$k = (h/SA).(Q_p/t).(1/\pi) \tag{1}$$

Then, after having calculated the desired laminate permeability $k$ from Equation 1, laboratory measurements are made to identify laminates having a permeability $k_o$ substantially equivalent to the calculated permeability $k$. The measurements are carried out by using a standard osmosis cell and measuring the rate of fluid flow through a laminate having a known composition and thickness. The flow rate is determined by measuring fluid transport from a first chamber containing a fluid free of agent through a laminate that separates it from a second chamber housing a solution containing a known concentration of agent that exhibits an osmotic gradient across the laminate. Sometimes the chamber contains an osmotically effective compound which is used as osmotic driving agent. The flow measurement is performed by adding to the first chamber the fluid and then adding to the second chamber, equipped with a stirring bar, the same fluid containing agent, and optionally containing the additional osmotic agents. The first chamber is connected through a conduit to a reservoir containing a supply of fluid and the second chamber is connected to a vertically positioned tube of known diameter and calibrated with indicia that indicate the amount of fluid in the tube. In operation, fluid flows from the first chamber through the laminate into the second chamber by osmosis causing the solution to rise in the tube over time, $t$, to give a volume displacement $\Delta v$, during a time interval $\Delta t$. The volume, $\Delta v$, is read on the tube calibrated in cm$^3$, and the time interval, $\Delta t$, is measured with a stopwatch. The value $k_o\pi$ in cm$^3$ mil/cm$^2$ hr for the laminate with permeability, $k_o$, for the agent solution with an osmotic pressure, $\pi$, is calculated from Equation 2, and wherein $A_o$ is the area of the laminate, in the osmosis cell, and $h_o$ is the thickness of this laminate.

$$k_o = (\Delta V/\Delta t).(h_o/A_o).(1/\pi) \tag{2}$$

If the measured value, $k_o$, approximates the calculated value, $k$, the laminate can be used for manufacturing the osmotic device.

The properties of laminae suitable for forming laminated walls also can be determined with the osmosis cell. These properties are integral parameters in controlling the release of an agent from systems, as properties of laminated walls such as permeability to fluids and resistance to passage of agents are the sum of all the properties of the individual laminae. These properties are expressed by Equation 3.

$$h_t/(k\pi)_t = h_1/(k\pi)_1 + h_2/(k\pi)_2 + \cdots h_n/(k)_2 \tag{3}$$

wherein $t$ is the laminated wall, 1, 2 and $n$ are laminae, $h_t$ is the thickness of the laminated wall, $h_1$, $h_2$ and $h_n$ are the thickness of the laminae, $(k\pi)_t$ is the fluid transmission rate for the laminated wall and it is the product of permeability of the laminated wall to fluid times the osmotic pressure, $(k\pi)_1$, $(k\pi)_2$ and $(k\pi)_n$ have a like meaning for their respective laminae. Other procedures and devices useful for measuring fluid permeability and osmotic flow are disclosed in *J. App. Poly. Sci.*, Vol. 9, pages 1341 to 1362, 1965; and in *Yale J. Biol. Med.*, Vol. 42, pages 139 to 153, 1970.

Suitable stabilizing materials can be selected from the above materials for blending with the lamina forming materials used to form a laminated wall buy those skilled in the art by using the procedures described below. These procedures are the lamina weight loss and the osmosis procedure. The procedures use lamina formed with stabilizers and formed without stabilizers. The lamina weight loss procedure is carried out with lamina that are cast from solution or optionally melt pressed. The lamina are solution cast with a Gardner film-casting knife on a clean glass plate at room temperature with the solution removed by evaporation in an oven at elevated temperatures until the lamina is dry. Next, the lamina is removed from the glass and cut into strips 1 to 10 cm in length, 1 to 10 cm in width and having a thickness of 1 to 10 mils. Then, after all the strips are cut to have the same area and weight, they are placed in a glass container filled with a solution consisting of a known concentration of agent formulated with the fluid of the environment of use. The temperature of the container is made to correspond to the temperature of the environment where an osmotic system formed with the lamina will be placed for releasing agents. At regular time intervals, strips are taken form the solution, rinsed in distillation water, dried in an oven, usually 50° C for 24 hours, and weighed. The weight of a single strip repeatedly introduced into the solution, or the weight of many strips consecutively removed at different time intervals are indicated along the ordinate, plotted as a function of time indicated along the abscissa, such as $t_1$, $t_2$, $t_3$, etc. as shown in FIG. 5. In FIG. 5, line 1 represents the results obtained for a lamina that maintains its physical and chemical integrity when exposed to agent solution. That is, the lamina does not lose any weight over time and demonstrates inertness and resistance to erosion in the presence of agent solution. In the same Figure, line 2 represents a lamina which upon exposure to agent solution, demonstrates a weight loss and is undesirable for making an inert portion of a laminated wall of an osmotic system. A stabilizer can be blended into this lamina to enhance its inertness and resistance and substantially prevent weight loss thereby making the lamina useful for fabricating laminated wall.

Figure 6:
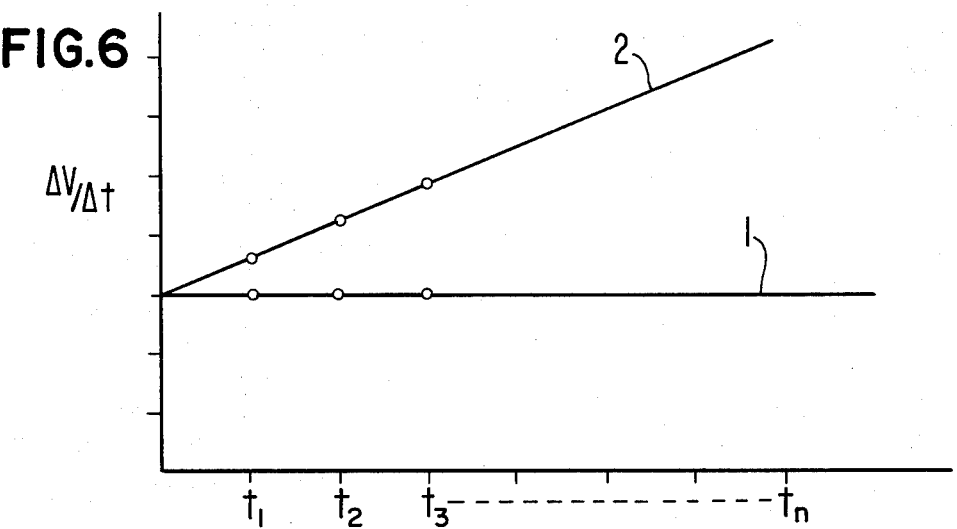
FIG. 6 is a graph comparing the fluid flux through a lamina that maintains its integrity in the presence of fluid with a lamina that slowly loses its integrity in the presence of fluid.

In the osmosis procedure, the rate of fluid flow through a lamina or laminate is measured and it is performed exposing the inert lamina to the test environment or agent by using an osmosis cell. The purpose of the procedure is to ascertain (1) if a given lamina, or the laminate, maintains its integrity in the presence of fluid and agent, and (2) if a stabilizer added to the lamina increases its physical and chemical integrity as seen from flux measurements. The procedure is carried out using the cell according to the above described procedure with the volume of solution, $\Delta V$, rising in the tube attached to chamber 2 measured and plotted as a function of time, $t$. The data obtaind for two different laminae are shown in FIG. 6. In FIG. 6, line 1 represents a lamina that maintains its integrity in the presence of fluid and agent. That is, since the rate of fluid flow is substantially constant, the lamina does not undergo any substantial change over time, $t$. Line 2 shows the fluid flux, $\Delta V/\Delta t$, through a lamina where the rate is continually increasing over time. This change indicates the lamina does not maintain its integrity in the presence of fluid or agent. For those applications where a change in flux is unwanted, a different lamina should be selected for the system or a stabilizer can be added to the lamina to enhance its inertness. The flux through laminae containing stabilizer is measured as just described. The properties of laminates also can be determined with the osmosis cell. Using the above techniques, one versed in the art would use the weight loss and osmosis procedures for ascertaining if the fluid and agent adversely affect the laminate or laminae, and also for determining if a stabilizer overcomes this effect. The stabilizer can be added in varying amounts to obtain an acceptable slope as seen in FIGS. 5 and 6, with the stabilizer decreasing the slope, not shown, indicating a lessening of laminate and laminae agent solution interaction.

Figure 7:
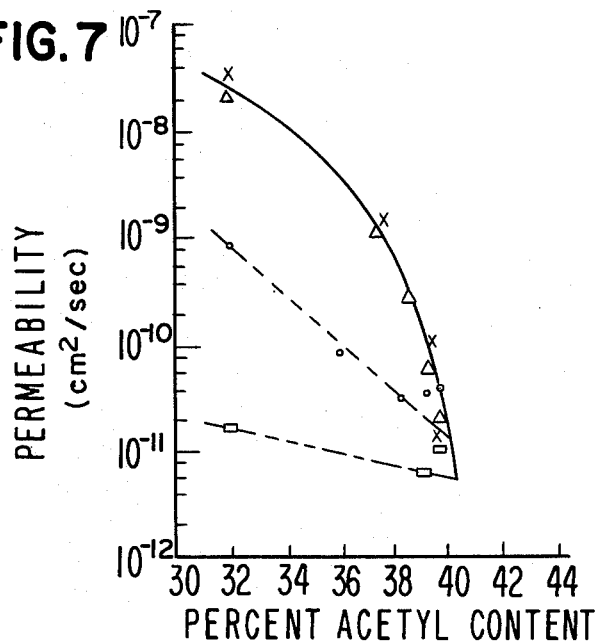
FIG. 7 is a graph representing the permeability of a series of lamina to a series of compounds; and, FIG. 8 represents the increase in fluid permeability of a material containing a flux enhancer.

Additional scientific criterions that can be used by those skilled in the art for selecting a stabilizing material include the following: (a) the material possesses a high degree of substitution, for example, the material has undergone etherification or esterification particularly acylation towards or to completion with lamina formed containing these stabilizers demonstrate increased resistance to hydrolysis and increased rejection of agent, (b) the stabilizer exhibits a flux decrease to fluid and solute with increasing molecular size of the substituting group, such as an ether or ester group, (c) the stabilizer exhibits a flux decrease proportional to the increase in size of the substituent, for example, the decrease occurs as the number of carbon atoms increase in a hydrocarbon moiety such as an alkyl or alkoxy moiety, (d) the stabilizer exhibits increased stability with an increase in the degree of substitution of hydrophobic ether and larger hydrophobic ester groups with an accompanying decrease in the degree of substitution of smaller hydrophilic ester groups, and (e) the stabilizer exhibits a flux decrease as the number of polar, ionic groups bonded to the stabilizer decrease. These principles are exemplified and illustrated in FIG. 7. FIG. 7 is an illustration of the decrease in polymer permeability to solutes, such as sodium chloride indicated by $x$, potassium chloride indicated by $\Delta$, magnesium sulfate indicated by O, and potassium sulfate indicated by $\square$, with increasing degrees of substitution by ester groups including acetyl moieties. A lower permeability to solutes signifies a higher rejection or exclusion of the solute from the polymer network, thereby diminishes the chances for polymer-solute interaction, while increasing the stability of the polymer. The trends shown in FIG. 7 for the indicated solutes hold for other agents.

The expressions "flux enhancing agent", "flux decreasing agent" and "flux regulator" as used herein means a compound that when added to semipermeable laminae forming material assists in regulating the fluid permeability or liquid flux through the laminae and the final laminated wall. The agent can be preselected to increase or decrease the liquid flow. Agents that produce a marked increase in permeability to fluid such as water, are often essentially hydrophilic, while those that produce a marked decrease to fluids such as water, are essentially hydrophobic. The flux regulators in some embodiments are can increase the flexibility of the laminae and the resulting laminated wall. The flux regulators in one embodiment, are polyhydric alcohols and derivatives thereof, such as polyalkylene glycols of the formula $H-(O-alkylene)_n-OH$ wherein the bivalent alkylene radical is straight or branched chain and has from 1 to 10 carbon atoms and $n$ is 1 to 500 or higher. Typical glycols include polyethylene glycols 300, 400, 600, 1500, 1540, 4000, and 6000 of the formula $H-(OCH_2CH_2)_n-OH$ wherein $n$ is respectively 5 to 5.7, 8.2 to 9.1, 125 to 13.9, 29 to 36, 29.8 to 37, 68 to 84, and 158 to 204. Other polyglycols include the low molecular weight glycols such as polypropylene, polybutylene and polyamylene.

The flux regulators in another embodiment include poly($\alpha,\omega$)-alkylenediols wherein the alkylene is straight or branched chain of from 2 to 10 carbon atoms such as poly(1,3)-propanediol, poly(1,4)-butanediol, poly(1,5)-pentanediol and poly(1,6)-hexanediol. The diols also include aliphatic diols of the formula $HOC_nH_{2n}OH$ wherein $n$ is from 2 to 10 and the diols are optionally bonded to a non-terminal carbon atom such as 1,3-butylene glycol, 1,4-pentamethylene glycol, 1,5-hexamethylene glycol and 1,8-decamethylene glycol; and alkylenetriols having 3 to 6 carbon atoms such as glycerine, 1,2,3-butantriol, 1,2,3-pentanetriol, 1,2,4-hexanetriol and 1,3,6-hexanetriol.

Other flux regulators include esters and polyesters of alkylene glycols of the formula $HO-(alkylene-O)_n-H$ wherein the divalent alkylene radical includes the straight chain groups and the isomeric forms thereof having from 2 to 6 carbons and $n$ is 1 to 14. The esters and polyesters are formed by reacting the glycol with either a monobasic or dibasic acid. Exemplary flux regulators are ethylene glycol dipropionate, ethylene glycol butyrate, ethylene glycol diacetate, triethylene glycol diacetate, butylene glycol dipropionate, polyester of ethylene glycol with succinic acid, polyester of diethylene glycol with maleic acid and polyester of triethylene glycol with adipic acid. Also, certain stabilizers in some embodiments can serve as a flux regulator particularly when it has a low D.S. of acyl moities.

Figure 8:
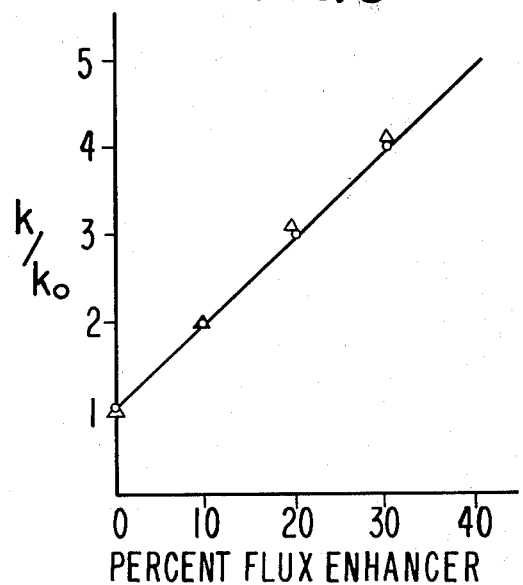

Suitable flux regulators for compounding with a material to increase or decrease its fluid permeability can be selected by blending known amounts of a regulator with the material, casting the blends into thin laminae, and then measuirng the change in permeability towards the fluid found in the environment of use. For example, to two separate batches of lamina forming cellulose acetate having an actyl content of 32% and 39.8% were added 1, 2 and 3 grams of flux regulator polyethylene glycol having a molecular weight of 400 and the ingredients blended in a high shear blender in the presence of 120 ml of dimethyl formamide to yield six blends. Next, the blends were solvent cast with a Gardner knife and dried in an oven for 7 days at 50° C. The water permeability of the six laminae was measured in the osmosis cell described above and the results recorded in FIG. 8. In FIG. 8, the triangles represent cellulose acetate 32% and the circles represent cellulose acetate 39.8%. Also, as recorded on the ordinate, $k_o$ indicates the water permeability through cellulose acetate 32% free of flux regulator and cellulose acetate 39.8% that did not contain any flux regulator, and $k$ indicates the water permeability through cellulose acetate 32% and cellulose acetate 39.8% where both contained the flux regulator. The positive integers 10, 20, 30 and 40 recorded on the abscissa, indicate the percent of flux regulator in the lamina. Using the above technique, specific flux regulators for blending with specific materials to regulate the permeability can be selected for making the desired lamina for making a laminated wall. The amount of flux regulator added to a material generally is an amount sufficient to produce the desired permeability, and it will vary according to the lamina forming material and the flux regulator used to modulate the permeability. Usually, from 0.001 parts up to 50 parts, or higher of flux regulator can be used to achieve the desired results, with a presently preferred range consisting of 0.1 part up to 30 parts of regulator or mixtures theeof for 100 parts of lamina forming material.

Exemplary plasticizers suitable for the present purpose generically include plasticizers that lower the temperature of the second-order phase transition of the laminae forming materials or the elastic modulus thereof, increase the workability of the laminae of the laminated wall, its flexibility and its permeability to fluid. Plasticizers operable for the present purpose include both cyclic plasticizers and acyclic plasticizers. Typical plasticizers are those selected from the group consisting of phthalates, phosphates, citrates, adipates, tartrates, sebacates, succinates, glycolates, glycerolates, benzoates, myristates, sulfonamides, and halogenated phenyls. Generally from 0.01 to 100 parts, or higher, of a plasticizer or a mixture of plasticizers are incorporated into 100 parts of lamina forming material.

Exemplary plasticizers further include dialkyl phthalates, dicycloalkyl phthalates, diaryl phthalates and mixed alkyl-aryl phthalates as represented by dimethyl phthalate, dipropyl phthalate, di(2-ethylhexyl)phthalate, di-isopropyl phthalate, diamyl phthalate and dicapryl phthalate; alkyl and aryl phosphates such as tributyl phosphate, trioctyl phosphate, tricresyl phosphate, trioctyl phosphate, tricresyl phosphate and triphenyl phosphate; alkyl citrate and citrate esters such as tributyl citrate, triethyl citrate, and acetyl triethyl citrate; alkyl adipates such as dioctyl adipate, diethyl adipate and di(2-methoxyethyl)adipate; dialkyl tartrates such as diethyl tartrate and dibutyl tartrate; alkyl sebacates such as diethyl sebacate, dipropyl sebacate and dinonyl sebacate; alkyl succinates such as diethyl succinate and dibutyl succinate; alkyl glycolates, alkyl glycerolates, glycol esters and glycerol esters such as glycerol diacetate, glycerol triacetate, glycerol monolactate diacetate, methyl phythayl ethyl glycolate, butyl phthalyl butyl glycolate, ethylene glycol diacetate, ethylene glycol dibutyrate, triethylene glycol diacetate, triethylene glycol dibutyrate and triethylene glycol dipropionate. Other plasticizers include camphor, N-ethyl-(o- and p-toluene) sulfonamide, chlorinated biphenyl, benzophenone, N-cyclohexyl-p-toluene sulfonamide, and substituted epoxides.

Suitable plasticizers can be selected for blending with the lamina forming materials by selecting plasticizers that have a high degree of solvent power for the materials, are compatible with the materials over both the processing and use temperature range, exhibit permanence as seen by a strong tendency to remain in the plasticized lamina, impart flexibility to the lamina, and are non-toxic to animals, humans, avians, fishes and reptiles. Procedures for selecting a plasticizer having the described characteristics are disclosed in the *Encyclopedia of Polymer Science and Technology*, Vol. 10, pages 228 to 306, 1969, published by John Wiley & Sons, Inc. Also, a detailed description pertaining to the measurement of plasticizer properties, including solvent parameters and compatibility, the Hildebrand solubility parameter $\delta$, the Flory-Huggins interaction parameter $\mu$, and the cohesive-energy density, CED, parameter is disclosed in *Plasticization and Plasticizer Processes, Advances in Chemistry Series* 48, Chapter 1, pages 1 to 26, 1965, published by the American Chemical Society. The amount of plasticizer added generally is an amount sufficient to produce the desired lamina and it will vary according to the plasticizer and the materials. Usually, about 0.001 part up to 50 parts, or higher, of plasticizer can be used for 100 parts of lamina forming material with a presently preferred range of 0.1 part to 20 parts of plasticizer, or mixtures thereof for 100 parts of lamina forming materials.

Dispersants useful for the present purpose are those dispersants when added to a lamina forming material and other materials aid in producing an integral composite that is useful for making the operative laminated wall of a system. The dispersants act by regulating the surface energy of materials to improve their blending into the composite. This latter material is used for manufacturing devices that maintain their integrity in the environment of use during the agent release period. Generally, the dispersants are amphipathic molecules comprised of a hydrophobic part and a hydrophilic part. The dispersants can be anionic, cationic, nonionic or amphoteric and they include anionics such as sulfated esters, amides, alcohols, ethers and carboxylic acids; sulfonated aromatic hydrocarbons, aliphatic hydrocarbons, esters and ethers; acylated amino acids and peptides; and metal alkyl phosphates; cationic dispersants such as primary, secondary, tertiary and quaternary alkylammonium salts; acylated polyamines; and salts of heterocyclic amines, arylammonium dispersants such as esters of polyhydric alcohols; alkoxylated amines; polyoxyalkylene; esters and ethers of polyoxyalkylene glycols; alkanolamine fatty acid condensates; tertiary acetylamic glycols; and dialkyl polyoxyalkylene phosphates; and ampholytics such as betamines; and amino acids.

Typical dispersants include polyoxyethylenated glycerol ricinoleate; polyoxyethylenated castor oil having from 9 to 52 moles of ethylene oxide; glycerol mannitan laurate, and glycerol(sorbitan oleates, stearates or laurates); polyoxyethylenated sorbitan laurate, palmitate, stearate, oleate or hexaolate having from 5 to 20 moles of ethylene oxide; mono- , di- and poly-ethylene glycol stearates, laurates, oleates, myristates, behenates or ricinoleates; propylene glycol carboxylic acid esters; sorbitan laurate, palmitate, oleate, and stearate; polyoxyethylenated octyl, nonyl, decyl, and dodecylphenols having 1 to 100 moles of ethylene oxide; polyoxyethylenated nonyl, lauryl, decyl, cetyl, oleyl and stearyl alcohols having from 3 to 50 moles of ethylene oxide; polyoxypropylene glycols having from 3 to 300 moles of ethylene oxide; sodium salt of sulfated propyl oleate; sodium di(heptyl)sulfosuccinate; potassium xylenesulfonate, 1:1 myristic acid diethanolamide; N-coco-$\beta$-aminopropionic acid; bis-(2-hydroxyethyl)tallowamine oxide; (diisobutylphenoxyethoxyethyl)dimethylbenzylammonium halide, N,N'-polyoxypropylenated ethylenediamine having a molecular weight from 500 to 3000; tetraalkylammonium salts with up to 26 carbon atoms in the cation; sodium or potassium salt of polypeptide cocoanut, oleic or undecylenic acid condensate; metal salts of N-acylated short chain aminosulfonic acids; soybean phosphatides; and sulfobetaine.

Suitable dispersants can be selected from the above and from other dispersants for blending with laminae forming materials by using the dispersant's hydrophile-lipophile balance number, HLB. This number represents the proportion between the weight percentages of hydrophilic and lipophilic groups in a dispersant. In use, the number indicates the behavior of the dispersant, that is, the higher the number the more hydrophilic the dispersant and the lower the number the more lipophilic the dispersant. The required HLB number for blending lamina forming materials is determined by selecting a dispersant with a known number, blending it with the materials and observing the results. A homogeneous composite is formed with the correct number; while a heterogeneous mixture indicates a different number is needed. This new number can be selected by using the prior number as a guide. The HLB number is known to the art for many dispersants, and they can be experimentally determined according to the procedure in *J. Soc. Cosmetic Chem.*, Vol. 1, pages 311 to 326, 1949, or it can be calculated by using the procedure in *J. Soc. Cosmetic Chem.*, Vol. 5, pages 249 to 256, 1954, and in *Am. Perfumer Essent. Oil Rev.*, Vol. 65, pages 26 to 29, 1955. Typical HLB numbers are set forth in Table 1. Generally a number of 10 or less indicates lipophilic behavior and 10 or more indicates hydrophilic behavior. Also, HLB numbers are algebraically additive. Thus, by using a low number with a high number, blends of dispersants can be prepared having numbers intermediate between the two numbers. The amount of dispersant needed is an amount that when blended with lamina forming materials will form the desired composite; this will vary according to the particular dispersant and materials that are blended to form the lamina. Generally, the amount of dispersant will range from about 0.001 parts up to 40 parts, or higher, for 100 parts of lamina forming material with a presently preferred range of 0.1 part to 15 parts of dispersant or mixtures thereof, for 100 parts of lamina forming material.

TABLE 1

| DISPERSANT | HLB NUMBER |
| --- | --- |
| Sorbitan trioleate | 1.8 |
| Polyoxyethylene sorbitol beeswax | 2.0 |
| Sorbitan tristearate | 2.1 |
| Polyoxyethylene sorbitol hexastearate | 2.6 |
| Ethylene glycol fatty acid ester | 2.7 |
| Propylene glycol fatty acid ester | 3.4 |
| Propylene glycol monostearate | 3.4 |
| Ethylene glycol atty acid ester | 3.6 |
| Glycerol monostearate | 3.8 |
| Sorbitan monooleate | 4.3 |
| Propylene glycol monolaurate | 4.5 |
| Diethylene glycol fatty acid ester | 5.0 |
| Sorbitan monopalmitate | 6.7 |
| Polyoxyethylene dioleate | 7.5 |
| Polyoxypropylene mannitol dioleate | 8.0 |

TABLE 1-continued

| DISPERSANT | HLB NUMBER |
| --- | --- |
| Sorbitan monolaurate | 8.6 |
| Polyoxyethylene lauryl ether | 9.5 |
| Polyoxyethylene sorbitan monolaurate | 10.0 |
| Polyoxyethylene lanolin derivative | 11.0 |
| Polyoxyethylene glycol 400 monooleate | 11.4 |
| Triethanolamine oleate | 12.0 |
| Polyoxyethylene nonyl phenol | 13.0 |
| Polyoxyethylene sorbitan monolaurate | 13.3 |
| Polyoxyethylene sorbitol lanolin | 14.0 |
| Polyoxyethylene stearyl alcohol | 15.3 |
| Polyoxyethylene 20 cetyl ether | 15.7 |
| Polyoxyethylene 40 stearate | 16.9 |
| Polyoxyethylene monostearate | 17.9 |
| Sodium oleate | 18.0 |
| Potassium oleate | 20.0 |

Exemplary solvents suitable for manufacturing the laminates and laminae include inert inorganic and organic solvents that do not adversely harm the materials and the final laminated wall. The solvents broadly include members selected from the group consisting of aqueous solvents, alcohols, ketones, esters, ethers, aliphatic hydrocarbons, halogenated solvents, cycloaliphatic, aromatics, heterocyclic solvents and mixtures thereof. Typical solvents include acetone, diacetone alcohol, methanol, ethanol, isopropyl alcohol, butyl alcohol, methyl acetate, ethyl acetate, isopropyl acetate, n-butyl acetate, methyl isobutyl ketone, methyl propyl ketone, n-hexane, n-heptane, ethylene glycol monoethyl ether, ethylene glycol monoethyl acetate, methylene dichloride, ethylene dichloride, propylene dichloride, carbon tetrachloride, nitroethane, nitropropane, tetrachloroethane, ethyl ether, isopropyl ether, cyclohexane, cyclooctane, benzene, toluene, naphtha, 1,4-dioxane, tetrahydrofuran, diglyme, water, and mixtures thereof such as acetone and water, acetone and methanol, acetone and ethyl alcohol, methylene dichloride and methanol, and ethylene dichloride and methanol.

The expression "passageway" as used herein comprises means and methods suitable for releasing the agent from the device. The expression includes an aperture, orifice or bore through the laminated wall formed by mechanical procedures or by eroding an erodible element, such as a gelatin plug, in the environment of use. A detailed description of osmotic passageways and the maximum and minimum dimensions for a passageway are disclosed in U.S. Pat. Nos. 3,845,770 and 3,916,899.

The osmotically effective compounds that can be used for the purpose of the invention include inorganic and organic compounds that exhibit an osmotic pressure gradient against an external fluid across the laminated wall of the system. The compounds are used mixed with an agent that has limited solubility in the external fluid with the compounds forming a saturated solution containing agent that is osmotically delivered from the system. The phrase "limited solubility" as used herein means the agent has a solubility of about less than 1% by weight in the external fluid. The compounds are used by homogenously or heterogenously mixing the compound or a mixture of compounds with an agent, either before they are charged into the reservoir, or by self-mixing after they are charged into the reservoir. In operation, these compounds attract fluid into the system producing a solution of compound which is delivered from the system concomitantly transporting undissolved and dissolved agent to the exterior of the system. Osmotically effective compounds useful for the present purpose include magnesium sulfate, magnesium chloride, sodium chloride, lithium chloride potassium sulfate, sodium carbonate, sodium sulfite, lithium sulfate potassium chloride, calcium bicarbonate, sodium sulfate, calcium sulfate, potassium acid phosphate, calcium lactate, d-mannitol, urea, inositol, magnesium succinate, tartaric acid, carbohydrates such as raffinose, sucrose, glucose, α-d-lactose monohydrate, and mixtures thereof. The compound is initially present in excess and it can be in any physical form such as particle, crystal, pellet, tablet, strip, film or granule. The osmotic pressure of saturated solutions of various osmotically effective compounds and for mixtures of compounds at 37° C, in water, is listed in Table 2. In the table, the osmotic pressure $\pi$, is in atmospheres, ATM. The osmotic pressure is measured in a commercially available osmometer that measures the vapor pressure difference between pure water and the solution to be analyzed, and according to standard thermodynamic principles, the vapor pressure ratio is converted into osmotic pressure difference. In Table 2, osmotic pressures of from 20 ATM to 500 ATM are set forth; of course, the invention includes the use of lower osmotic pressures from zero, and higher osmotic pressures than those set forth by way of example in Table 2. The osmometer used for the present measurements is identified as Model 302B, Vapor Pressure Osmometer, manufactured by the Hewlett Packard Co., Avondale, Penna.

TABLE 2

| COMPOUND OR MIXTURE | OSMOTIC PRESSURE ATM |
|---|---|
| Lactose-Fructose | 500 |
| Dextrose-Fructose | 450 |
| Sucrose-Fructose | 430 |
| Mannitol-Fructose | 415 |
| Sodium Chloride | 356 |
| Fructose | 355 |
| Lactose-Sucrose | 250 |
| Potassium Chloride | 245 |
| Lactose-Dextrose | 225 |
| Mannitol-Dextrose | 225 |
| Dextrose-Sucrose | 190 |
| Mannitol-Sucrose | 170 |
| Sucrose | 150 |
| Mannitol-Lactose | 130 |
| Dextrose | 82 |
| Potassium Sulfate | 39 |
| Mannitol | 38 |
| Sodium Phosphate Tribasic . 12H$_2$O | 36 |
| Sodium Phosphate Dibasic . 7H$_2$O | 31 |
| Sodium Phosphate Dibasic . 12H$_2$O | 31 |
| Sodium Phosphate Dibasic Anhydrous | 29 |
| Sodium Phosphate Monobasic . H$_2$O | 28 |

The expression "active agent" as used herein broadly includes any compound, composition of matter or mixture thereof, that can be delivered from the system to produce a beneficial and useful result. The agent can be soluble in a fluid that enters the reservoir and functions as an osmotically effective solute or it can have limited solubility in the fluid and be mixed with an osmotically effective compound soluble in fluid that is delivered from the system. The active agent includes pesticides, herbicides, germicides, biocides, algicides, rodenticides, fungicides, insecticides, anti-oxidants, plant growth promoters, plant growth inhibitors, preservatives, disinfectants, sterilization agents, catalysts, chemical reactants, fermentation agents, foods, food supplements, nutrients, cosmetics, drugs, vitamins, sex sterilants, fertility inhibitors, fertility promoters, air purifiers, microorganism attenuators, and other agents that benefit the environment of use.

In the specification and the accompanying claims, the term "drug" includes any physiologically or pharmacologically active substance that produces a localized or systemic effect or effects in animals, including mammals, humans and primates, avians, domestic household, sport or farm animals such as sheep, goats, cattle, horses and pigs, for administering to laboratory animals such as mice, rats and guinea pigs, and to fishes, reptiles and zoo animals. The active drug that can be delivered includes inorganic and organic compounds without limitation, those materials that act on the central nervous system such as hypnotics and sedatives, including pentobarbital sodium, phenobarbital, secobarbital, thiopental and mixtures thereof, heterocyclic hypnotics such as dioxopiperidines and glutarimides, hypnotics and sedatives such as amides and ureas, exemplified by diethylisovaleramide and α-bromoisovaleryl urea, hypnotic and sedative urethanes and disulfanes, psychic energizers such as isocarboxazid, nialamide, phenelzine, imipramine, tranylcypromine and pargylene, tranquilizers such as chloropromazine, promazine, fluphenazine, reserpine, deserpidine, meprobamate, benzodiazepines such as chlordiazepoxide, anticonvulsants such as primidone, enitabas, diphenylhydantoin, ethltion, pheneturide and ethosuximide, muscle relaxants and antiparkinson agents such as mephenesin, methocarbomal, trihexylphenidyl, biperiden, levo-dopa also known as L-dopa and L-$\beta$-3-4-dihydroxypehnylalanine, analgesics such as morphone, codeine, meperidine, nalorphine, antipyretics and anti-inflammatory agents such as aspirin, salicylamide, colchicine and sodium salicylamide, local anesthetics such as procaine, lidocaine, naepaine, piperocaine, tetracaine and dibucane, antispasmodics and muscle contractants such as atropine, scopolamine, methscopolamine, oxyphenonium, papaverine, prostaglandins such as PGE$_1$, PGE$_2$, PGF$_{1\alpha}$, PGF$_{2\alpha}$ and PGA, anti-microbials such as penicillin, tetracycline, oxytetracycline, chlorotetracycline, chloramphenicol and sulfonamides, anti-malarials such as 4-aminoquinolines, 8-aminoquinolines and pyrimethamine, hormonal agents such as prednisolone, cortisone, cortisol and triamcinolone, androgenic steroids such as methyltestosterone, and fluoxesterone, estrogenic steroids such as 17$\beta$-estradiol, α-estradiol, estriol, α-estradiol 3-benzoate, and 17-ethynyl estradiol-3-methyl ether, progestational steroids such as progesterone, 19-nor-pregn-4-ene-3,20-dione, 17-hydroxy-19-nor-17-α-pregn-5(10)-ene-20-yn-3-one, 17α-ethynyl-17-hydroxy-5(10)-estren-3-one, and 9$\beta$,10α-pregna-4,6-diene-3,20-dione, sympathomimetic drugs such as epinephrine, amphetamine, ephedrine and norepinephrine, cardiovascular drugs such as procainamide, procainamide hydrochloride, amyl nitrile, niroglycerin, dipyredamole, sodium nitrate and mannitol nitrate, diuretics such as chlorathiazide, acetazolamide, methazolamide and flumethiazide, antisparasitics such as bephenium, hydroxynaphthoate, dichlorophen and dapsone, neoplastics such as mechlorethamine, uracil mustard, 5-fluorouracil, 6-thioguanine and procarbazine, hypoglycemic drugs such as insulin, isophane insulin, protamine zinc insulin suspension, globin zinc insulin, extended insulin zinc suspension, tolbutamide, acetohexamide, tolazamide and chlorpropamide, nutritional agents such as ascorbic acid, niacin, nicotinamide, folic acid, choline, biotin, pantothenic acid, and vitamin B$_{12}$, essential amino acids, essential fats, eye drugs such as pilocarpine, pilocarpine salts such as pilocarpine nitrate, pilocarpine hydrochloride, dichlorphenamide, atropine, atropine sulfate, scopolamine and eserine salicylate, and electrolytes such as calcium gluconate, calcium lactate, potassium chloride, potassium sulfate, sodium chloride, potassium fluoride, sodium fluoride, ferrous lactate, ferrous gluconate, ferrous sulfate, ferrous fumurate and sodium lactate. The beneficial drugs are known to the art in *Remington's Pharmaceutical Sciences*, 14th Ed., 1970, published by Mack Publishing Co., Easton, Penna.; and in *The Pharmacological Basis of Therapeutics*, by Goodman and Gilman, 4th Ed., 1970, published by The MacMillian Company, London.

The drug can also be in various forms, such as uncharged molecules, molecular complexes, pharmacologically acceptable salts such as hydrochlorides, hydrobromides, sulfate, laurylate, palmitate, phosphate, nitrate, borate, acetate, maleate, tartrate, oleate, and salicylate. For acidic drugs, salts of metals, amines or organic cations, for example quaternary ammonium can be used. Derivatives of drugs such as esters, ethers and amides which have solubility characteristics suitable for use herein can be used alone or mixed with other drugs. Also, a drug that is water insoluble can be used in a form that is a water soluble derivative thereof to effectively serve as a solute, and on its release from the device, is converted by enzymes, hydrolyzed by body pH or other metabolic processes to the original form, or to a biologically active form. The agent can be in the reservoir as a solution, dispersion, paste, cream, particle, granule, emulsion, suspension or powder. Also, the agent can be mixed with a binder, dispersant, emulsifier or wetting agent and dyes.

The amount of agent present in the system is initially in excess of the amount that can be dissolved in the fluid that enters the reservoir. Under this physical state when the agent is in excess, the system will osmotically operate to give a substantially constant rate of release. The rate of agent release pattern can also be varied by having different amounts of agent in the reservoir to form solutions containing different concentrations of agent for delivery from the device. Generally, the system can house from 0.05 ng to 5 grams or more, with individual systems containing for example, 25 ng, 1 mg, 5 mg, 250 mg, 500 mg, 1.5 g, and the like.

The solubility of an agent in an external fluid can be determined by various art known techniques. One method consists in preparing a saturated solution comprising the external fluid plus the agent as ascertained by analyzing the amount of agent present in a definite quantity of the fluid. A simple apparatus for this purpose consists of a test tube of medium size fastened upright in a water bath maintained at constant temperature and pressure, for example, one atmosphere, in which the fluid and agent are placed and stirred by a motor driven rotating glass spiral. After a given period of stirring, a definite weight of the fluid is analyzed and the stirring continued for an additional period of time. If the analysis shows no increase of dissolved agent after successive periods of stirring, in the presence of excess solid agent in the fluid, the solution is saturated and the results are taken as the solubility of the product in the fluid. If the agent is soluble, an added osmotically effective compound optionally may not be needed; if the agent has limited solubility in the fluid, then an osmotically effective compound can be incorporated into the device. Numerous other methods are available for the determination of the solubility of an agent in a fluid. Typical methods used for the measurement of solubility are chemical analysis, ultra violet spectometry, density, refractive index and electrical conductivity. Details of various methods for determining solubilities are described in *United States Public Health Service Bulletin*, No. 67 of the Hygienic Laboratory; *Encyclopedia of Science and Technology*, Vol. 12, pages 542 to 556, 1971, published by McGraw-Hill, Inc.; and *Encyclopaedic Dictionary of Physics*, Vol. 6, pages 547 to 557, 1962, published by Pergamon Press, Inc.

The systems of the invention are manufactured by standard techniques. For example, in one embodiment, the agent and other ingredients that may be housed in the compartment and a solvent are mixed into a solid, semisolid or gel form by conventional methods such as ballmilling, calendering, stirring, or rollmilling and then pressed into a preselected shape. The laminae forming devices system can be applied by molding, spraying or dipping the pressed shape into wall forming materials. In another embodiment, the laminae can be cast into films, shaped to the desired dimensions, an exterior lamina sealed to an interior lamina to define a compartment that is filled with agent and then closed. The system also can be manufactured with an empty compartment that is filled through the passageway. The system when formed of more than one laminate, joined by various joining techniques such as high frequency electronic sealing that provides clean edges and firmly sealed systems. Another, and presently preferred, technique that can be used to apply laminae to a compartment is the air suspension procedure. This procedure consists in suspending and tumbling the pressed agent in a current of air and a lamina composition until the lamina is applied to the agent. The procedure is repeated with a different lamina to form the laminate. The air suspension procedure is described in U.S. Pat. No. 2,799,241; *J. Am. Pharm. Assoc.*, Vol. 48, pages 451 to 459, 1959; and ibid, Vol. 49, pages 82 to 84, 1960. Other standard manufacturing procedures are described in *Modern Plastics Encyclopedia*, Vol. 46, pages 62 to 70, 1969; and in *Pharmaceutical Sciences*, by Remington, Fourteenth Edition, pages 1626 to 1678, 1970, published by Mack Publishing Company, Easton, Penna.

The following examples are merely illustrative of the present invention, and they should not be considered as limiting the scope of the invention in any way, as these examples and other equivalents thereof will become apparent to those versed in the art in the light of the present disclosure, the drawings and the accompanying claims.

EXAMPLE 1

An osmotic therapeutic system for delivering ascorbic acid at an osmotically controlled rate was manufactured as follows: first, 200 grams of ascorbic acid was slowly added to 10 grams of ethylcellulose in 100 milliliters of isopropyl alcohol and the materials blended for 45 minutes to produce wet granules. The granules were dried at 50° C for 48 hours and then passed through a No. 20 mesh sieve. Then, the granules were lubricated with 1% magnesium stearate by mixing in a blender and after 30 minutes of blending they were passed through a No. 20 sieve. The granules were then pressed into a solid mass using a standard tableting machine and a ⅝ inch diameter punch. The compressed mass had a finished hardness of 7.1 kg as measured by a Strong-Cobb hardness tester. Each mass contained 450 mg of ascorbic acid, and had a total area of 2.6 cm$^2$.

Next, a lamina forming composition identified as $h_1$ was prepared by thoroughly blending in a high shear blender for 50 minutes a batch comprising 29% cellulose acetate having an acetyl content of 38.3%, 61% cellulose acetate having an acetyl content of 32%, and 10% polyethylene glycol having a molecular weight of 400 dissolved in an acetone:water solvent formulation having a 90:10 weight-to-weight ratio to produce a homogeneous composite.

Then, the compressed masses were placed in a Wurster air suspension machine and each mass coated with lamina $h_1$ until it had a lamina 3 mils thick. The vlaue for $k\pi_1$ was 0.14 cm$^3$.mil/cm$^2$.hr.

A second lamina forming composition, identified as $h_2$ was prepared by thoroughly blending in a high shear blender the following constituents: 90% cellulose acetate having an acetyl content of 32%, and 10% polyethylene glycol having a molecular weight of 400 dissolved in a 90 parts acetone to 10 parts water solvent, weight-to-weight, for 50 minutes to produce a 5% polymeric composite.

Next, the total exposed surface of lamina $h1$ distant from the ascorbic acid was laminated in the Wurster machine with lamina forming composite $h_2$ until lamina $h_2$ had a thickness of 2 mils. The flux transmission, $k\pi_2$ was 0.22 cm$^3$.mil/cm$^2$.hr. The resulting laminated wall, comprised of laminae $h_1$ and $h_2$, had a thickness, $h_t$, of 5 mils and a $k\pi_t$ of 0.16 cm$^3$.mil/cm$^2$.hr. An osmotic passageway was drilled through the laminated wall for releasing ascorbic acid from the compartment. The passageway had a diameter of 10 mils and the device had a rate of release of 30 mg per hour.

EXAMPLE 2

A plurality of osmotic drug delivery systems are manufactured according to the procedure of Example 1 wherein the conditions were as described except that the drug of Example 1 is replaced with an orally administrable drug selected from the group consisting of methazolamide, ethoxyolamide, diazepan, amitriptylene hydrochloride, imipramine hydrochloride, naicin, benzthiazide, chorothiazide, tolbutamide, tolazamide, chloropropamide, procainamide hydrochloride, colchicine, and atropine.

EXAMPLE 3

A plurality of osmotic drug delivery systems are manufactured according to the procedures of Examples 1 and 2 with all conditions as described except that lamina $h_1$ was replaced with a lamina selected from the group of laminae consisting of cellulose acetate propionate, cellulose acetate butyrate, cellulose acetate benzoate and celluslose acetate ethylcarbamate.

EXAMPLE 4

An osmotic therapeutic system manufactured in the form of an oral, osmotic device for releasing the lysine salt of acetylsalicylic acid in the gastrointestinal tract was made as follows: first, 450 mg of the salt was compressed by a standard technique with a ⅜ inch punch into a compressed mass having a total area of 2.9 cm$^2$. The mass was then surrounded with a laminated wall comprised of inner and outer laminae.

The inner lamina was a composite formed of a blend of 90% nonerodible, inert cellulose acetate having an acetyl content of 39.8%, and 10% polyethylene glycol having a molecular weight of 400. This blend was dissolved in acetone to form a 5% solution, by weight. The compressed mass of lysine salt was then coated with the cellulose acetate/polyethylene glycol blend according to the air suspension technique described in J. Pharm. Sci., Vol. 53, No. 8, pages 877 to 881, 1964, and ibid, Vol. 53, No. 8, pages 953 to 955, 1964. The dried inner lamina had a thickness $h_1$ of 0.5 mils and a $k\pi_1$ of 0.03 cm$^3$.mils/cm$^2$.hr.

Next, an outer lamina that maintains its integrity in the environment of use, and consisting of polymeric cellulose acetate having an acetyl content of 32% was laminated onto the exposed surface of lamina $h_1$ to form an integral laminated wall that surrounded the drug compartment. The cellulose acetate was intimately laminated to lamina $h_1$ from a blend consisting of 90% cellulose acetate having an acetyl content of 32% and 10% polyethylene glycol having a molecular weight of 400 in acetone:water in the proportion of 88.5:11.5, weight-to-weight. The outer lamina $h_2$ had a thickness of 4.0 mils and a $k\pi_2$ of 0.19 cm$^3$.mils/cm$^2$.hr.

The laminated wall, $h_t$, of the system had a thickness of 4.5 mils. An osmotic passageway was drilled through the wall and it had a diameter of 9 mils. The system had a controlled and continuous rate of release of 40 mg/hr with a variation of about ±3 to 5% over a prolonged period of time.

EXAMPLE 5

A plurality of osmotic drug delivery systems are manufactured according to the procedure of Example 4 with all conditions as described except the lamina forming material in $h_1$ is replaced with a member selected from the group consisting of cellulose propionate having a propionyl content of 38.5%, cellulose acetate propionate having an acetyl content of 1.5 to 7% and a propionyl content of 39 to 42%, and cellulose acetate butyrate having an acetyl content of 13 to 15% and a butyryl content of 34 to 39%.

EXAMPLE 6

The procedure of Example 4 is repeated in this example with all conditions as previously described except that lamina $h_2$ in this example is a semipermeable homopolymer comprising 100% cellulose acetate having an acetyl content of 32%.

EXAMPLE 7

The procedure of Example 4 is repeated in this example and all conditions are as described except the system is sized, shaped and adapted to an ocular therapeutic system and the drug in the compartment is replaced with an ophthalmic drug that is a member selected from the group consisting of idoxuridine, phenylephrine, pilocarpine hydrochloride, eserine, carbachol, phospholine iodine, demecarium bromide, cyclopentolate, homatropine, scopolamine and epinephrine.

EXAMPLE 8

An oral, osmotic system for releasing theophylline monoethanolamine over a six to seven hour therapeutic period is manufactured as follows: first, a multiplicity of compressed drug cores are formed in a conventional Manesty tableting machine for lamination. The machine uses a 5/16 inch diameter concave punch to produce compressed cores having hardness of about 8.42 kg as measured by a Strong-Cobb hardness tester. The cores have an area of about 1.63 cm$^2$. The cores contained 125 mgs of theophylline, present as the monoethanolamine, 8.74 mgs of binder polyvinylpyrrolidone and 1.58 mgs of lubricant magnesium stearate. The cones were placed in a Wurster air suspension machine that air tumbled the cores until they are uniformly coated with a laminated wall. The laminated wall has an inner lamina facing the drug compartment and an outer lamina distant from the compartment.

The laminae are consecutively coated with the Wurster machine to form an integral, laminated wall. The inner lamina is coated from a blend made by adding (1) a mixture of 68.1% cellulose acetate having an acetyl content of 38.3% and 12.76% polyethylene glycol having a molecular weight of 400 dissolved in a solvent consisting of 80 parts of methylene chloride and 20 parts of methanol, to (2) a mixture of 17.02% hydroxybutyl methylcellulose and 2.12% polyoxypropylene glycol having a molecular weight of 950 dissolved in 80 parts of methylene chloride and 20 parts of methanol. The two mixtures were thoroughly blended and then an additional solvent was added that consisted of 90 parts of acetone and 10 parts of water. All the materials were stirred for 30 minutes. The inner lamina $h_1$ had a thickness of 0.5 mils and a $k\pi_1$ of 0.052 cm$^3$.mils/cm$^2$.hr.

The outer lamina was permanently laminated onto lamina $h_1$ from a blend prepared as follows: to a first mixture consisting of 76.6% cellulose acetate having an acetyl content of 32% and 12.76% polyethylene glycol having a molecular weight of 400 dissolved in a solvent consisting of 80 parts of methylene chloride and 20 parts of methanol were added a second mixture with continuous stirring. The second mixture consisted of 8.51% hydroxybutyl methylcellulose and 2.12% of polyoxypropylene glycol having a molecular weight of 950 dissolved in a solvent consisting of 80 parts of methylene chloride and 20 parts of methanol. The stirring continued until the two mixtures were thoroughly blended. Then, an additional solvent, consisting of 90 parts of acetone and 10 parts of water, was added to the blend and all the materials stirred for 30 minutes until a homogeneous composite was formed. The applied laminae had a thickness $h_2$ of 4.5 mils and a $k\pi_2$ of 0.22 cm$^3$.mil/cm$^2$.hr.

Finally, a 10 mil aperture was mechanically drilled through the laminated wall to produce the osmotic system. The laminated wall had a thickness $h_t$ of 5 mils and a $k\pi_t$ of 0.166 cm$^3$.mils/cm.$^2$.hr. The system had a release rate of 20 mgs/hr over a prolonged period of time.

EXAMPLE 9

The procedure of Example 8 is repeated but the drug in the compartment is replaced with a member selected from the group consisting of nicotinamide, mannitol hexanitrate, isocarboxyazid, triamcinolone, salicylamide, aspirin and aminophylline.

EXAMPLE 10

An osmotic, therapeutic system for the controlled and continuous oral release of the beneficial agent sodium acetazolamide is made as follows: first, 170 grams of sodium acetazolamide and 8.5 grams of 5% polyvinylpyrrolidone in isopropyl alcohol are blended in a standard V-blender for 45 minutes to produce wet granules. The granules are dried in an oven at 50° C for 48 hours and passed through a standard No. 30 mesh sieve. Then, 1.8 grams of magnesium stearate were separately passed through the No. 30 sieve and the granules were mixed with the magnesium stearate in the blender for about 30 minutes, or until a uniform mixture is obtained. The mixture is then compressed in a conventional Manesty machine using a 5/16 inch diameter concave punch to produce drug cores. The cores have a hardness of about 9 kg, as measured by a Strong-Cobb hardness tester. The cores contain 125 mgs of acetazolamide and have an area of 1.4 cm$^2$.

The laminated wall is prepared as follows: first, an inner lamina, $h_1$, forming blend is prepared by blending 90% cellulose acetate having an acetyl content of 38.3% and 10% polyethylene glycol having a molecular weight of 400 in sufficient acetone to produce a 5% polymeric solution.

Next, an outer lamina, $h_2$, forming blend is prepared by blending 90% cellulose acetate having an acetyl content of 32% and 10% polyethylene glycol having a molecular weight of 400 in sufficient solvent consisting of acetone:water in the ratio of 90:10 weight-to-weight. The materials were blended as described to produce a 5% polymeric solution.

Then, the drug cores prepared as above were placed in a Wurster air suspension machine. The cores were air tumbled until they were uniformly coated with the inner lamina forming solution. The coated cores were dried in an oven at 50° C for one week to evaporate the solvent. Next, the dried cores are returned to the Wurster machine and coated with the outer lamina forming solution. The laminated product was dried as described. Finally, a 7.5 mil passageway was mechanically drilled through the laminated wall. The inner lamina $h_1$ had a thickness of 1.5 mils and a $k\pi_1$ of 0.103 cm$^3$.mil/cm$^2$.hr. The outer lamina $h_2$ had a thickness of 4 mils and a $k\pi_2$ of 0.38 cm$^3$.mils/cm$^2$.hr. The laminated $h_t$ had a thickness of 5.5 mils and a $k\pi_t$ of 0.21 cm$^3$.mil/cm$^2$.hr. The system had a controlled and continuous rate of release of about 20 mgs per hour over a prolonged period of time.

EXAMPLE 11

The procedure of Example 10 is repeated with all lamination procedures as described, but the drug in the compartment is replaced with a member selected from the group consisting of calcium gluconate, calcium lactate, potassium sulfate, potassium fluoride, sodium fluoride, ferrous lactate, ferrous gluconate, ferrous sulfate, ferrous fumurate, and sodium lactate, which drugs are released in an effective amount at a controlled and continuous rate over a prolonged period of time.

EXAMPLE 12

An osmotic therapeutic system for releasing sodium fluoride at an osmotically controlled rate was made as follows: first, 26.6 grams of sodium fluoride, consisting of cubic and tetragonal crystals, were mixed with 173.4 grams of mannitol to produce 200 grams of a homogeneous dispersion. Then, 170 grams of the dispersion and 8.5 grams of 5% polyvinylpyrrolidone in isopropyl alcohol were blended in a standard V-blender for 45 minutes to produce wet granules. The granules were dried in an oven at 50° C for 48 hours and passed through a standard No. 30 mesh sieve. Then, 2.0 grams of magnesium stearate were passed through the No. 30 sieve and the granules mixed with the magnesium stearate in the blender for about 30 minutes. The mixture was then added to a Manesty machine and drug cores pressed using a 0.375 inch diameter concave punch to produce compressed drug cores. The cores have a hardness of about 8.5 kg as measured by the Strong-Cobb hardness tester. Each compressed mass had an area of 2.12 cm$^2$ and weighed 305 mgs. Each mass was then surrounded with a laminated wall as follows: first, an inner lamina $h_1$ was prepared by blending 170 grams of cellulose acetate having an acetyl content of 32% with 30 grams of polyethylene glycol having a molecular weight of 400 in sufficient solvent consisting of acetone:water in the ratio of 90:10 weight-to-weight and the materials blended to produce 5% lamina forming solution.

Next, an outer lamina $h_2$ forming blend was prepared by blending 170 grams of cellulose acetate having an acetyl content of 38.3% and 30 grams of polyethylene glycol having a molecular weight of 400 in acetone and the materials blended as described to produce a 5% polymeric solution.

Next, the cores were placed in a Wurster air suspension machine and air tumbled until the cores were uniformly coated with the inner lamina forming solution. The coated cores were dried in an oven at 50° C for one week to evaporate the solvent. Then, the dried cores were returned to the machine, and the cores again tumbled until they were coated uniformly with the outer lamina forming solution, $h_2$, was permanently laminated thereto to form laminated wall $h_t$. The laminated product was dried as described. Finally, an 8 mil aperture was drilled through the laminated wall.

The inner lamina $h_1$ had a thickness of 3 mils and a $k\pi_1$ of 0.25 cm$^3$.mils/cm$^2$.hr. The outer lamina $h_2$ had a thickness of 1 mil and a $k\pi_2$ of 0.05 cm$^3$.mil/cm$^2$.hr. The laminated wall had a thickness of 4 mils and a $k\pi_t$ of 0.125 cm$^3$.mils/cm$^2$.hr. The system had a controlled and continuous rate of release of 2.5 mgs/hr of sodium fluoride over a prolonged period of time.

EXAMPLE 13

An osmotic therapeutic system manufactured in the form of an oral, osmotic device for releasing potassium chloride in the gastrointestinal tract was made as follows: first, 500 mgs cores of potassium chloride were compressed by standard technique with a 0.375 inch punch into a solid mass having an area of 2.3 cm$^2$. Each mass was then surrounded with a laminated wall comprised of an inner and outer laminae. The inner lamina was formed of non-erodible, inert, 70 minutes hydrolyzed semipermeable polyvinyl acetate applied by the air suspension techniques described in *J. Pharm. Sci.,* Vol. 53, No. 8, pages 877 to 881, 1964, and ibid, Vol. 53, No. 8, pages 953 to 955, 1964. A 5% polymer solution in ethanol:water in the ratio of 95:5 volume-to-volume was used to form the lamina. The lamina $h_1$ had a thickness of 2 mils and a $k\pi_1$ of 0.1 cm$^3$.mil/cm$^2$.hr.

Next, an outer lamina $h_2$ forming blend was prepared by blending 270 grams of cellulose acetate having an acetyl content of 32% and 30 grams of polyethylene glycol having a molecular weight of 400 in sufficient solvent consisting of acetone:water and in the ratio of 90:10 weight-to-weight and the materials blended to produce a 5% solution.

Then, the outer lamina $h_2$ was laminated onto lamina $h_1$ according to the procedure described in Example 12. Lamina $h_2$ had a thickness of 3 mils and a $k\pi_2$ of 0.54 cm$^3$.mil/cm$^2$.hr. A 9 mil aperture was drilled through the laminated wall. The laminated wall $h_t$ had a thickness of 5 mils and a $k\pi_t$ of 0.195 cm$^3$.mils/cm$^2$.hr. The system had a rate of release of 30 mgs per hour.

EXAMPLE 14

An osmotic therapeutic system for delivering NaCl at an osmotically controlled rate was manufactured according to the procedures of Examples 1, 10 and 12 with all conditions as described, except that the laminated wall surrounding the compartment comprised three laminae in laminar arrangement. The lamina facing the drug compartment, $h_1$ consists of semipermeable 90 minutes partially hydrolyzed polyvinyl acetate. The lamina had a thickness of 2 mils and a $k\pi_1$ of 0.3 cm$^3$.mil/cm$^2$.hr. The second lamina $h_2$ was laminated to lamina $h_1$ and it consists of 40% cellulose acetate having an acetyl content of 38.3%, 40% cellulose acetate having an acetyl content of 32%, and 20% polyethylene glycol having a molecular weight of 400. Lamina $h_2$ had a thickness of 2 mils and a $k\pi_2$ of 0.46 cm$^3$.mil/cm$^2$.hr. The third lamina $h_3$ distant from the compartment, consists of 90% cellulose acetate having an acetyl content of 32% and 10% polyethylene glycol 400. Lamina $h_3$ had a thickness of 1 mil and a $k\pi_3$ of 0.5 cm$^3$.mil/cm$^2$.hr. The laminated wall $h_t$ comprised of $h_1 + h_2 + h_3$, had a thickness of 5 mils and a $k\pi_t$ of 0.385 cm$^3$.mil/cm$^2$.hr. A 10 mil aperture through $h_t$ released NaCl at the rate of 55 mgs/hr, with a variation of ± 5% over a prolonged period of time.

EXAMPLE 15

An osmotic ocular therapeutic system for the delivery of pilocarpine nitrate at a rate of 103 μg/hr from a system having a laminated wall with a total area of 1.2 cm$^2$ and a thickness of 3 mils, with the pilocarpine nitrate having a solubility of 250 mg/ml in water, and designed in the form of an elliptical shaped device is constructed as follows: to a drug core of pilocarpine nitrate is applied from dimethyl formamide, a 1 mil thick $h_1$ lamina of inert semipermeable poly(urethane) to yield an inner lamina having a $k\pi_1$ of 0.36 × 10$^{-3}$ cm$^3$.mil/cm$^2$.hr. Next, to the total outer surface of $h_1$ is applied from a 5% solution in acetone: water, in the ratio of 90:10 weight-to-weight a 2 mil thick $h_2$ lamina of semipermeable inert blend of 50% cellulose acetate having an acetyl content of 32% and 50% cellulose acetate having an acetyl content of 38.3%. Lamina $h_2$ had a $k\pi_2$ of 0.018 cm$^3$.mil/cm$^2$.hr. The laminated wall has an aperture of 6.9 mils. The laminated wall $h_t$ has a $k\pi_t$ of 1 × 10$^{-3}$ cm$^3$.mil/cm$^2$.hr, and the system when placed in the cul-de-sac of an adult human eye, administers 103 μg/hr.

EXAMPLE 16

A series of oral osmotic therapeutic systems are manufactured using the above procedures. Each system comprises a laminated wall having a pair of laminae formed of a blend of semipermeable materials, with the laminae facing the compartment, the inner laminae, exposed to agent, having an increased acetyl content for the series. The results obtained indicated the inner laminae in the presence of agents KCl, NaCl, MgSO$_4$ and K$_2$SO$_4$ are substantially non-erodible and inert, and the laminae have increased rejection to the passage of agent as the percent acetyl content increases in the laminae. The measured permeability results for this system are set forth in FIG. 7. In FIG. 7, the numbers on the abscissa represent the percent acetyl content for the laminae exposed to agents. The numbers on the left ordinate represent the permeability of the laminae to the passage of agents. Also, the letter $x$ indicates the lamina was exposed to KCl, a triangle indicates the lamina was exposed to NaCl, the squares indicate the lamina was exposed to MgSO$_4$ and the circle indicates the lamina was exposed to K$_2$SO$_4$.

The novel osmotic devices of this invention use means for the obtainment of precise release rates in the environment of use while simultaneously maintaining the integrity of the device. While there has been described and pointed out features of the invention as applied to presently preferred embodiments, those skilled in the art will appreciate that various modifications, changes, additions, and omissions in the devices illustrated and described can be made without departing from the spirit of the invention.

We claim:

1. An oral osmotic system for dispensing a drug to the gastrointestinal tract of an animal, said system comprising:

a. a shaped, laminated wall having a permeability to fluid expressed by the equation:

$$k = \frac{h}{SA} \cdot \frac{Q_p}{t} \cdot \frac{1}{\pi}$$

wherein $K$ is the permeability of the wall to fluid present in the tract, $Q_p$ is the amount of drug delivered from the system in time $t$, $A$ is the area of the system, $h$ is the thickness of the laminated wall, $S$ is the solubility of drug in fluid imbibed into the system and $\pi$ is the osmotic pressure of drug in the system, the laminated wall comprising (1) a lamina formed of a semipermeable material that is permeable to the passage of fluid and impermeable to the passage of drug, and which material comprises the formula:

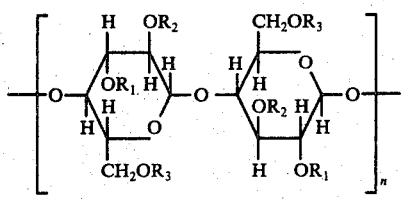

wherein $R_1$, $R_2$, and $R_3$ are independently selected from the group consisting of hydrogen and acyl with at least one of $R_1$, $R_2$, and $R_3$ an acyl group and $n$ is at least 5, said semipermeable material blended with a flux regulator that governs the lamina's permeability to fluid and it is a member selected from the group consisting of a polyhydric alcohol, polyalkylene glycol, poly($\alpha,\omega$)-alkylenediol, aliphatic diol and an ester of an alkylene glycol, and (2) a lamina that maintains its physical and chemical integrity during the dispensing of drug, the lamina comprising a semipermeable material that is permeable to the passage of drug and impermeable to the passage of drug, said material having the formula:

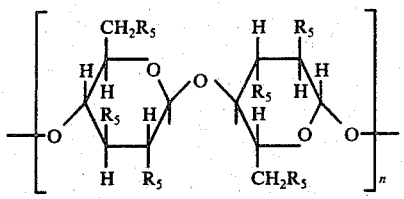

wherein $R_5$ is a member selected from the group consisting of alkyl, alkoxy, alkylcarbonate, alkylcarbamate, alkylsulfamate and acyloxy and $n$ is at least 5, said material blended with at least one of a member selected from the group consisting of a flux regulator that governs the permeability of the lamina to fluid and a plasticizer that lowers the second-order phase transition temperature of the lamina forming material;

b. the laminated wall surrounding and forming a compartment containing a drug selected from the group consisting of locally and systemically acting drugs;

c. a passageway in the wall communicating with the compartment and the exterior of the system for dispensing drug from the system; and, d. wherein in operation when the system is in the gastrointestinal tract, fluid therefrom is imbibed through the laminated wall into the compartment in a tendency towards osmotic equilibrium at a rate determined by the permeability of the laminated wall and the osmotic pressure gradient across the laminated wall, thereby forming a solution containing drug which is dispensed at a controlled rate through the passageway over a prolonged period of time.

2. The osmotic system for dispensing a drug according to claim 1, wherein the flux regulator in lamina (1) is a member selected from the group consisting of polyethylene glycol; 1,3-butylene glycol; 1,4-pentamethylene glycol; 1,5-hexamethylene glycol; 1,8-decamethylene glycol; glycerine; 1,2,3-butanetriol; 1,2,3-pentanetriol; poly (1,6)-hexamediol; poly(1,5)-pentanediol; and mixtures thereof.

3. The osmotic system for dispensing a drug according to claim 1, wherein lamina (1) contains a dispersant that regulates the surface energy of the materials in the lamina, and which dispersant is a member selected from the group consisting of sorbitan trioleate, sorbitan tristerate, glycerol monosterate, sorbitan monoleate, propylene glycol monolaurate, sorbitan monopalmitate, polyoxyethylene dioleate, sorbitan monolaurate, polyoxyethylene sorbitan monolaurate, polyoxyethlene glycol monolaurate, polyoxyethylene nonyl phenol, polyethylene cetyl ether, sodium oleate, and potassium oleate.

4. The osmotic system for dispensing a drug according to claim 1, wherein lamina (1) contains a plasticizer selected from the group consisting of dimethyl phthalate, dipropyl phthalate, di(2-ethylhexyl)phthalate, diisopropyl phthalate, diamyl phthalate, glycerol diacetate, triethylene glycol dibutyrate, and ethylene glycol dipropionate.

5. The osmotic system for dispensing a drug according to claim 1, wherein lamina (2) contains a plasticizer that is a different plasticizer than in lamina (1), and which plasticizer in lamina (2) is a member selected from the group consisting of tributyl citrate, triethyl citrate, acetyl triethyl citrate, dioctyl adipate, diethyl tartrate, dibutyl tartrate, diethyl sebacate, dipropyl sebacate, dinonyl sebacate, diethyl succinate, and dibutyl succinate.

6. The osmotic system for dispensing a drug according to claim 1, wherein lamina (2) contains a dispersant that is a member selected from the group consisting of polyoxytehylenated castor oil having from 9 to 52 moles of ethylene oxide; sodium di(heptyl) sulfosuccinate; potassium xylenesulfonate; 1:1 myristic acid diethanolamide; N-coco-$\beta$-aminopropionic acid; bis-(2-hydroxyethyl) tallowamine oxide; polyoxypropylene glycol having from 3 to 300 moles of ethylene oxide; and polyoxyethylene sorbitol beeswax.

7. The osmotic system for dispensing a drug according to claim 1, wherein the compartment contains an osmotically effective compound that exhibits an osmotic pressure gradient across the laminated wall against the fluid and which compound is a member selected from the group consisting of magnesium sulfate, magnesium chloride, sodium chloride, lithium chloride, potassium sulfate, sodium carbonate, sodium sulfite, lithium sulfate, potassium chloride, calcium carbonate, sodium sulfate, calcium sulfate, potassium acid phosphate, calcium lactate and magnesium succinate.

8. The osmotic system for dispensing a drug according to claim 1, wherein lamina (2) contains a dispersant that has a hydrophile-lipophile balance number from 1 to 20 and the lamina contains from 0.1 part to 15 parts of dispersant for 100 parts of said lamina.

9. An oral osmotic system for dispensing a drug to the gastrointestinal tract of an animal, said system comprising:

a. a shaped, laminated wall having a permeability to fluid expressed by the equation:

$$k_o = (\Delta V/\Delta t \cdot (h_o/A_o(1/\pi)$$

wherein $k_o$ is the permeability of the laminated wall to the passage of fluid, $\Delta V$ is the change in volume displacement through the laminated wall in time interval $\Delta t$, $h_o$ is the thickness of the laminated wall, $A_o$ is the area of the laminated wall and $\pi$ is the osmotic pressure of the drug in solution, the laminated wall comprising (1) a wall formed of a multiplicity of materials including a semipermeable material permeable to the passage of fluid and impermeable to drug, said material selected from the group consisting of cellulose acylates, cellulose diacylates and cellulose triacylates and compounded with at least one member selected from the group consisting of a stabilizer, flux enhancer, dispersant, plasticizer and mixtures thereof, and (2) a wall formed of a semipermeable material that is permeable to the passage of fluid and impermeable to the passage of drug which wall provides mechanical support for the other wall that comprises the laminated wall;

b. the laminated wall surrounding and forming a compartment containing a drug that on release from the system produces a beneficial result;

c. a passageway in the laminated wall communicating with the compartment and the exterior of the system for dispensing drug from the system; and, d. wherein in operation, when the system is in the gastrointestinal tract, fluid therefrom is imbibed through the laminated wall into the compartment in a tendency towards osmotic equilibrium at a rate determined by the permeability of the laminated wall and the osmotic pressure gradient across the laminated wall, thereby forming a solution containing drug which is dispensed at a controlled rate through the passageway over a prolonged period of time.

10. The osmotic system for dispensing a drug according to claim 9, wherein the drug is a nutritional drug selected from the group consisting of ascorbic acid, niacin, nicotinamide, folic acid, choline, biotin, pantothenic acid, vitamin $B_{12}$, and mixtures thereof.

11. The osmotic system for dispensing a drug according to claim 9, wherein the drug is an electrolyte selected from the group consisting of ferrous lactate, ferrous gluconate, ferrous sulfate, ferrous fumurate and mixtures thereof.

12. The osmotic system for dispensing drug according to claim 9, wherein the drug compartment contains 0.05 ng to 5 g of drug, which drug has limited solubility in fluid imbibed into the compartment and is present in the compartment with a member selected from the group consisting of an organic and inorganic osmotically effective solute that exhibits an osmotic pressure gradient across the wall against the fluid.

13. The osmotic system for dispensing a drug according to claim 9, wherein the wall formed of a multiplicity of materials faces the compartment and contains a stabilizer that has ungone esterification and etherification towards completion to impart physical and chemical stability to the wall in the presence of fluid and drug in the compartment.

14. The osmotic system for dispensing a drug according to claim 9, wherein the wall formed of a multiplicity of materials contains a member selected from the group consisting of cellulose trivalerate, cellulose trilaurate, cellulose tripalmate, cellulose trisuccinate, cellulose triheptylate, cellulose tricaprylate, cellulose trioctanoate, cellulose tripropionate, cellulose disuccinate, cellulose dipalmitate, cellulose dioctanoate, cellulose dicaprylate, cellulose dipentanate, cellulose acetate valerate, cellulose acetate succinate, cellulose propionate succinate, cellulose acetate octanoate, cellulose valerate palmitate, cellulose acetate palmitate and cellulose acetate heptanoate.

15. The oral, osmotic system for dispensing a drug according to claim 9, wherein the laminated wall is formed by tumbling a given mass of pressed drug in a current of air containing a multiplicity of wall forming materials and a solvent until a wall is applied to the drug; then, repeating the procedure by tumbling the walled drug in a current of air containing a different wall forming material and a solvent until another wall surrounds the drug, thereby forming the laminated semipermeable wall.

* * * * *